(12) United States Patent
Ghandi et al.

(10) Patent No.: US 11,382,188 B2
(45) Date of Patent: Jul. 5, 2022

(54) SYSTEMS AND METHODS FOR USE AND MEASUREMENT OF NON-THERMAL EFFECTS OF MICROWAVE RADIATION

(71) Applicant: University of Guelph, Guelph (CA)

(72) Inventors: Khashayar Ghandi, Eden Mills (CA); Pooya Afaghi, Moncton (CA)

(73) Assignee: University of Guelph

( * ) Notice: Subject to any disclaimer, the term of this patent is extended or adjusted under 35 U.S.C. 154(b) by 475 days.

(21) Appl. No.: 16/487,625

(22) PCT Filed: Feb. 21, 2018

(86) PCT No.: PCT/IB2018/000211
§ 371 (c)(1),
(2) Date: Aug. 21, 2019

(87) PCT Pub. No.: WO2018/154382
PCT Pub. Date: Aug. 30, 2018

(65) Prior Publication Data
US 2020/0068672 A1     Feb. 27, 2020

Related U.S. Application Data

(60) Provisional application No. 62/461,626, filed on Feb. 21, 2017.

(51) Int. Cl.
H05B 6/68    (2006.01)
A23L 3/01    (2006.01)
A61N 5/02    (2006.01)
B01J 19/12   (2006.01)

(52) U.S. Cl.
CPC ............... H05B 6/68 (2013.01); A23L 3/01 (2013.01); A61N 5/02 (2013.01); B01J 19/126 (2013.01); B01J 2219/1209 (2013.01)

(58) Field of Classification Search
CPC .... A61N 5/02; H05B 6/68; A23L 3/01; A23L 2/12; B01J 19/126; B01J 2219/1209; B01J 2219/123
USPC ....... 219/702, 687, 678, 679, 746, 748, 749, 219/745, 763, 757; 435/173.8, 255.7, 435/173.2, 173.1, 800, 29, 287.1; 426/273; 99/451; 422/108, 119
See application file for complete search history.

(56) References Cited

U.S. PATENT DOCUMENTS

| 5,962,054 A | 5/1999 | Kozempel et al. |
| 2008/0128410 A1* | 6/2008 | Bravo ............... H05B 6/782 219/687 |
| 2014/0249345 A1* | 9/2014 | Benke ............... G21F 9/001 588/1 |

FOREIGN PATENT DOCUMENTS

CN    2568134 Y    8/2003

OTHER PUBLICATIONS

International Searching Authority, International Search Report.
International Searching Authority, Written Opinion of the International Searching Authority, dated Jul. 12, 2018.

* cited by examiner

*Primary Examiner* — Quang T Van

(57) ABSTRACT

Microwave systems and new applications of microwave in medical, chemical and materials manufacturing and processing, food and health industries as well as in analytical chemistry instrumentation for in situ study of microwave effects are provided. In the case of medical applications, the microwave based damage is conducted in a way to diminish ablating or damaging the collateral tissue and to increase the probability of procedure achievement.

21 Claims, 26 Drawing Sheets

FIG. 10

SYSTEMS AND METHODS FOR USE AND MEASUREMENT OF NON-THERMAL EFFECTS OF MICROWAVE RADIATION

RELATED APPLICATIONS

The present patent document claims the benefit of the filing date under 35 U.S.C. § 119(e) of Provisional U.S. Patent Application Ser. No. 62/461,626 filed on Feb. 21, 2017, which hereby incorporated by reference.

BACKGROUND

1. Technical Field

The disclosed embodiments are related to microwave technologies and more particularly to systems and method for delivering and measuring non-thermal effects of microwave energy.

2. Background

Microwave assisted chemical reactions, microwave assisted hyperthermia therapeutic applications including assisted chemotherapy, and, in the food industry, microwave enhanced processes from food preparation to food preservation have enjoyed tremendous success and importance. In chemical reactions, microwave heating has been shown to dramatically improve yield, reaction rates, and provide enhanced physicochemical properties along with the evolvement of new material phases. In therapeutic applications, microwave heating has been used in hyperthermia therapies alone or in combination with other therapies for treating cancers and other severe ailments. In food processing, microwave heating has been used in a wide variety of applications from sterilization to cooking and preparing food products.

In all three of the above categories, microwave applications are based on the thermal heating effects of microwaves, using continuous sources. Non-thermal microwave effects (NTMEs) have been attributed to changes in reaction rates and/or selectivity, as well as therapeutic or other beneficial outcomes under microwave irradiation which cannot be rationalized by thermal effects. That is, NTMEs necessitate that the microwave effect is not just due to an increase in temperature of the medium (solvent or matrix where the solute is embedded in), but due to the non-thermal electric and magnetic field interactions of the microwave radiation with matter. The specific microwave effects (SPEs) are those which are characterized by the selective transfer of energy to certain solutes by microwave radiation.

There is significant controversy in the scientific literature regarding NTME's, with numerous reports for and against their existence. Previous patents, such as U.S. Pat. No. 5,962,054, disclose the use of non-thermal microwave effects to increase the shelf-life of liquid foods using NTME to reduce the population of microbial contamination, while patents such as U.S. Pat. No. 4,327,180 describe the use of NTME's by controlling the temperature using a liquid heat sink for tissues and biological samples to achieve desired biological outcomes under continuous microwave irradiation.

However, in these applications, thermal heating of the samples, tissues, and foods still occurs and may cause adverse effects. For example, in biological samples, elevated temperatures can result in burns, cell apoptosis due to excessive heat, protein and enzyme denaturation etc.

Many of these prior applications restricted heating to an increase of temperature between of 37° C. to 40° C., are only applicable to liquid samples, use continuous microwave sources, and generally do not apply microwave irradiation at high powers to limit the thermal impact upon the sample. For example, many microwave ablative therapies restrict microwave power to 40-65 watts (W). Despite this relatively low power, there are reports that microwave ablation could lead to temperatures of more than 150° C.

In food processing, short time exposures are used to limit undesirable thermal processing of raw food samples at full microwave power (>1100W), however it was shown that these are not sufficient to have a meaningful impact upon reducing the bacterial population on the surface of the food before thermal processing (cooking) occurs. Studies have however shown that the microwave power can have an impact upon bacteria such as E.coli, which is dependent upon the microwave power.

SUMMARY

As will be described in greater detail below, the instant disclosure describes systems and methods utilizing non-thermal effects of microwave radiation. Embodiments use pulsed MW irradiation while controlling the temperature of a sample using combination of using appropriate pulse structure/sequence for microwave and cooling fluids or other cooling devices, and efficient heat exchange mediums to expose materials, biological and food samples to NTME's while minimizing the thermal microwave effects. Beyond controlling using a cooling system, control of the pulse width/sequence, allows a high level of microwave radiation to be used without causing excessive heating. This is done with in-situ temperature and microwave measurements and in-situ spectroscopy under the same conditions for microwave on and off to have a system that has the same environment, temperature profile and geometry to compare microwave on and off effects to evaluate the true NTMEs.

Also described are the simultaneous irradiation of samples with both non-thermal MW irradiation and particle or ion beams, for medical therapies and other applications.

In one example, a method of controlling the temperature of a target material while subjecting the material to microwave irradiation is disclosed. The method includes measuring the temperature of the target and its surroundings, applying a variable length microwave pulse to the target, actively cooling the target, and adjusting the variable length microwave pulse and the active cooling of the target dependent on the measured temperature to achieve a desired temperature.

In another example, a non-thermal microwave device includes a variable pulse width microwave source operable to provide a variable width microwave pulse to a target, a temperature monitoring probe operable to measure the temperature of a target, a cooling system operable to control the temperature of the target, and a control circuit operable to adjust the pulse width and the cooling system to maintain a temperature measured by the temperature monitoring probe.

In another example, a pulsed microwave tool includes a temperature probe for real-time, and in situ or indirect measurements of a temperature of a target, a cooling system for cooling the target, a microwave generator operable to generate a variable pulse width microwave with appropriate variable pulse timings and sequences in response to the temperature of the target, a microwave antenna in the middle of the tool, and a cylindrical cooling jacket at the top with inlet and outlet to circulate cooling liquid in order to control the temperature of the target and cool down material adjacent the target.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

FIG. 10 is a screenshot of exemplary microwave controller software

Figure 1:
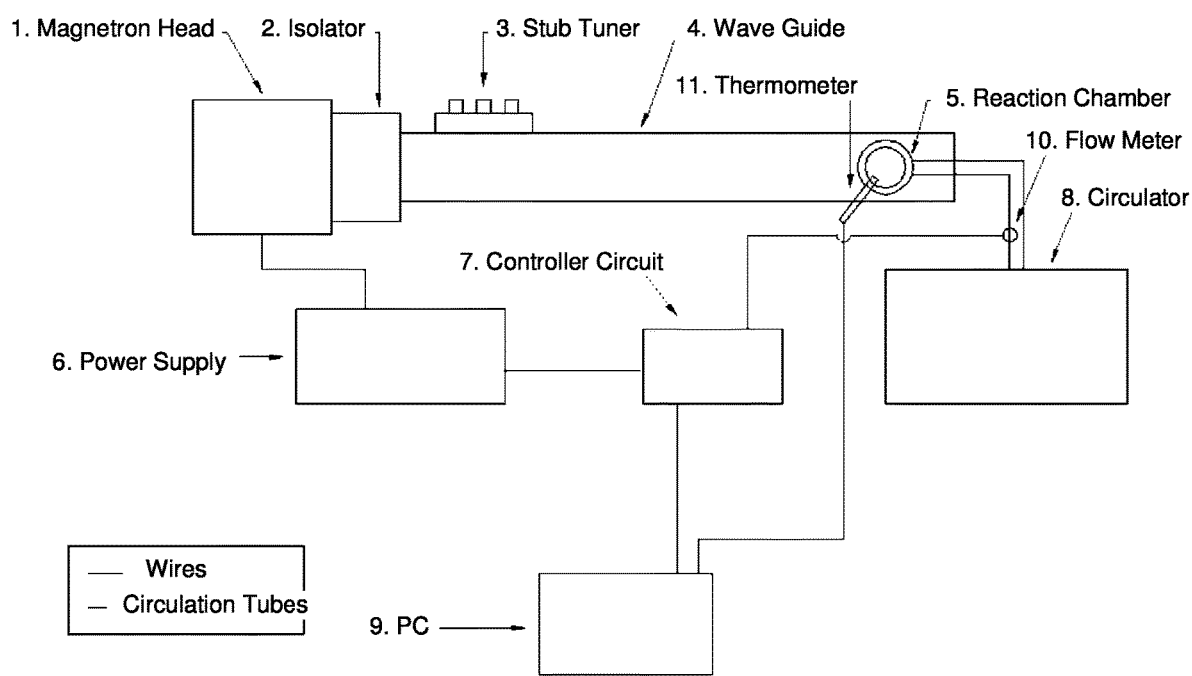
FIG. 1 is a schematic diagram of a microwave apparatus and setups

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

The present disclosure is generally directed to apparatuses, systems, and methods for non-thermal use of microwave energy. As will be explained in greater detail below, embodiments of the instant disclosure may include a microwave source, a microwave controller, and a cooling system.

Example methods include maintaining samples at room temperature or lower, while simultaneously exposing the sample to high microwave power to minimize adverse thermal effects of heating the sample. To that end, the method includes a combination of control of microwave pulse structure, sequences and different methods of cooling at the same time to control the temperature of the sample of the microwave irradiated material at a controlled temperature, including at temperatures under 0 C, while exposing the material to very intense pulses of microwave energy of the order of magnitude of 1,000 W. Exemplary applications include the combination of ion beams and electron beams with microwaves for therapeutic applications. Moreover, the microwave pulse sequences allow an intense microwave pulse (independent of temperature; due to efficient temperature control via feed-back system and pulse structure), followed by another weak pulse for measuring the effects of microwaves on cell kill rate in the case therapeutic/sterilizing applications.

An exemplary design of a microwave apparatus is presented below with experimental observations. Various modifications and embodiments of the apparatus and associated methods as would be apparent to one skilled in the art, as defined by the claims herein, are within the intended scope of the disclosure.

Examples of such modifications include but are not limited to the use of microwave antennas, probes, or other well-known means of delivering microwave radiation such as waveguides and coaxial cables. As well as cavity design changes to accommodate larger/smaller samples, and heat exchange surfaces, probes, active cooling fluids such as cooled N2/helium/CO2/Argon etc. fall within the spirit of the disclosure.

Figure 2:
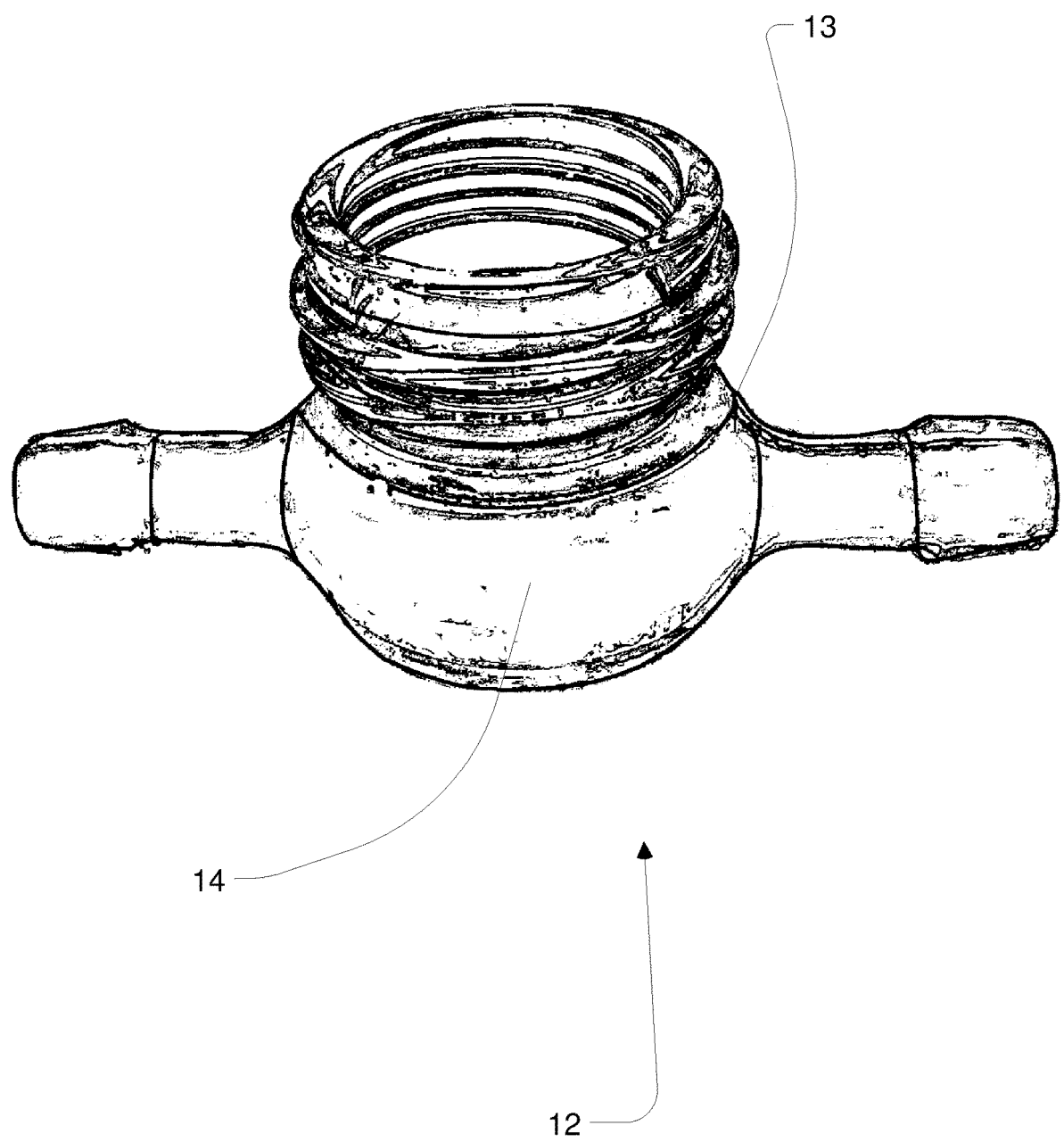
FIG. 2 is an example of a microwave sample cell.
Figure 3:
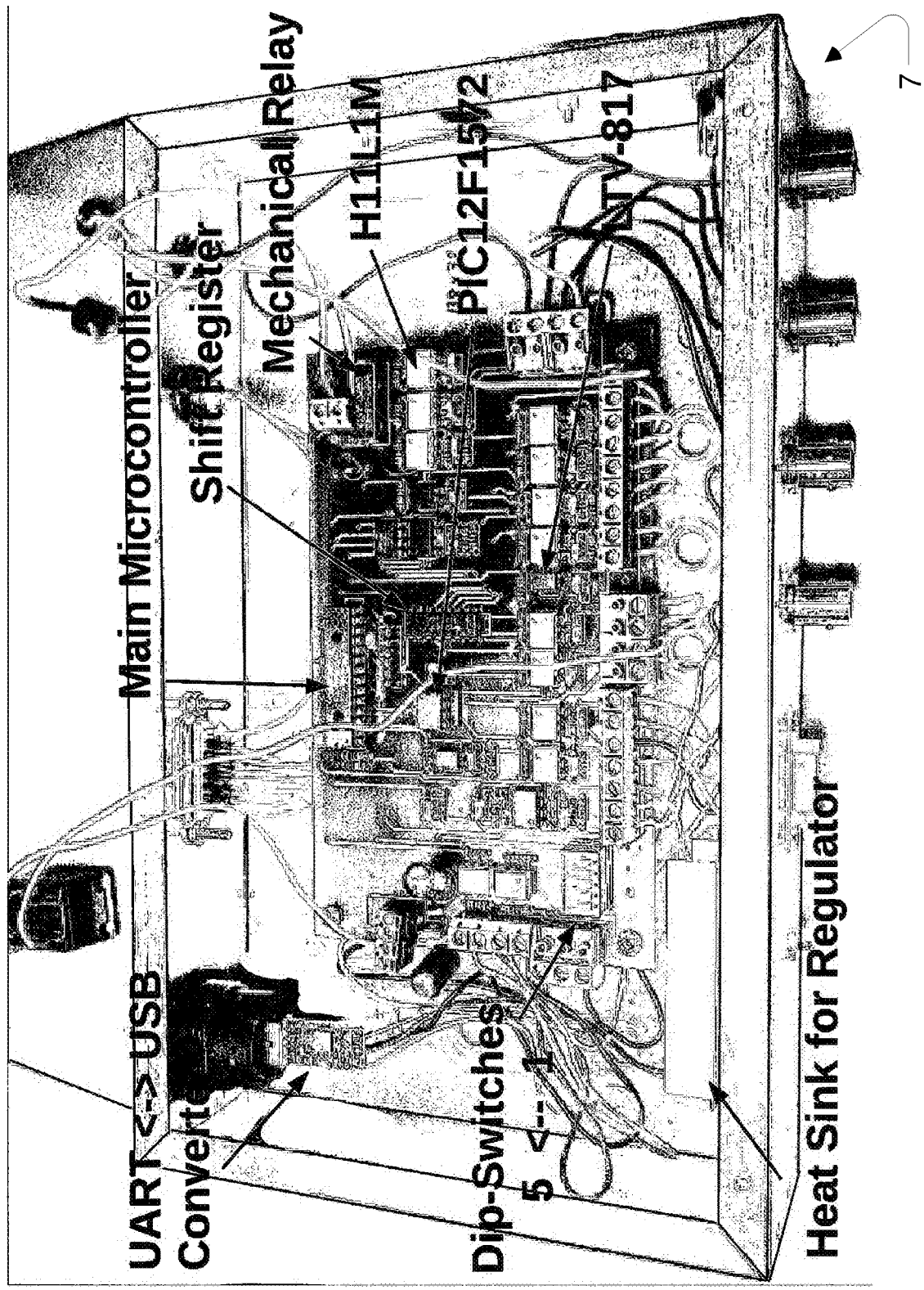
FIG. 3 is an example of an inside of a microwave controller circuit box.

As described by FIGS. 1-3, in on example, a microwave apparatus 11 includes a magnetron head 1, an isolator 2, a stub tuner 3, and a waveguide 4. Magnetron head 1 may be a 1000-Watt microwave generator operating at 2.45 GHz. Waveguide 4 includes an applicator portion including a reaction chamber 5 configured to house a sample. Applicator portion includes a cooling fluid inlet port and a cooling fluid outlet port. Applicator portion further includes temperature probe ports for monitoring temperature of a sample in reaction chamber 5. The ports communicate with tubes containing cooling fluid and are located at locations in waveguide 4 that minimize and/or eliminate any leakage of microwave radiation. Waveguide 4 may further include a window allowing simultaneous, or discontinuous irradiation of a sample contained in reaction chamber 5 by particle beam radiation, such as muons, neutrons etc.

FIG. 2 illustrates an example of a sample cell 12 for use in reaction chamber 5. Sample cell 12 has an active cooling sheath 13 through which cooling fluid is circulated, a sample cavity 14, a fiber optic temperature probe inlet, and a cap and O-ring system to seal the sample within as detailed by FIG. 2.

Cooling fluid in cooling sheath 13 is circulated through a suitable heat exchanger 8, using tubes passing through the inlet/outlet ports of the applicator portion of waveguide 4. In this specific example, heat exchanger may be a temperature controlled circulator, such as those available from Julabo Labortechnik, with a water/ethylene glycol mixture as the cooling fluid. The temperature is varied as needed to achieve a final desired temperature during microwave operation. In other embodiments, the cooling fluid may be silicon oils, water/ethylene glycol mixtures, liquid, or cooled gasses such as nitrogen, or argon.

In other embodiments, the sample cell may not contain an isolated cooling sheath, but instead include a single sample chamber through which the cooling fluid directly contacts the sample for temperature control. In still other embodiments, the sample cell may include a flowing sample that is pre-cooled before entering a location for microwave irradiation.

EXAMPLE USES

Embodiments may be used to further understand and exploit NTME effects in biological samples, as well as exploit new therapies and treatments using NTME's in conjunction with particle beams, ionizing beams, and high frequency and intense ionizing photon beams.

In the field of food preparation and processing, embodiments may be used to extend the shelf life of food by exposing meats and other solid foods to high power microwave radiation without the heating effects. Using conventional methods, this is not achievable with short duration exposure before cooking occurs. Thus, embodiments may be used to mitigate the irreversible thermal effects in raw foods, while improving shelf life, and reducing microbial contamination through the ability to expose the samples for larger time limits at higher microwave powers. Many current sterilization techniques depend upon thermal effects for sterilization, resulting in the inability to sterilize raw food, without cooking, or significant alteration of its nutrient profile. This is similarly applicable to liquid foods, where nutrients might decompose at higher temperatures, including those as high as 40 C.

Further uses of embodiments include providing new conditions for synthesis and manufacturing in the chemical and materials industry.

EXAMPLES

Example 1. Description of One Microwave Apparatus

As described by FIG. 1, a schematic description of the microwave apparatus, includes Magnetron head 1, an isolator 2 to prevent reflected microwave radiation from returning to the magnetron head 1, a tuner 3, and a waveguide 4 including necessary ports to accommodate cooling and temperature probe ports. Waveguide may further include a gas inlet port through which inert gasses such as nitrogen may be introduced to maintain a moisture or oxygen free microwave cavity. Additionally, the apparatus includes sample cell 12 and an electronic control circuit 7. Sample cell 12 as depicted by FIG. 2 contains a cooling sheath 13 surrounding sample chamber 14 as well as a temperature probe inlet and a cap and O-ring system to seal the sample within as required.

Electronic control circuit 7 is depicted in FIG. 3, contains various microcontrollers, shift registers, dip switches and other components to interface with a personal computer, and a main magnetron power supply, allowing an operator through a software interface to control the power and duration of continuous or pulsed microwaves emitted by magnetron head 1, as well as the time intervals between pulses. The electronic control circuit 7 additionally connects to various safety interlocks throughout the microwave apparatus, such as those placed between waveguide 4 and tuner 3, or a water flow sensor and others as required to ensure that the microwave pulses cannot be active until the apparatus is safely assembled and all components are working as desired (i.e. parts connected and assembled appropriately to ensure no leakage of microwave radiation, sufficient cooling water flow to ensure no damage to magnetron head 1, flow of cooling fluid through sample sheath 13 to prevent sample damage etc.) thus preventing any safety accidents or unintended leakage of microwave radiation.

Example 2. Controlling of the Temperature of Liquid and Solid Samples

In one example use of the apparatus of FIG. 1, various liquid and solid samples may be placed in sample cell 12 and exposed to pulsed microwave irradiation from magnetron head 1 while monitoring the temperature of the sample using a fiber optic probe. By manipulation of the set-temperature and flow rate of the cooling fluid, as well as the microwave pulse structure, it is possible to control the temperature of the sample while subjecting the sample to high powered microwave irradiation for an extended period of time (hours). In one example, a selection of samples at different microwave powers and their stable temperature under microwave irradiation are summarized in table 1 shown below. An aqueous solution of hydrogen peroxide, octanol, and a solid sample of magnesium oxide powder were maintained at temperatures at or well below room temperature while subject to microwave irradiation at high powers. Given the available equipment, the lowest cooling was achieved using octanol by maintaining it at −5 Celsius under 500 W of microwave power. The combination of the example design for the sample cell 12, cooling system, accurate temperature measurements, and microwave pulses timing and structure enable subzero temperatures during application of the microwave power. Aqueous solutions were able to be cooled to 11.5° C. for extended time duration (hours) while subject to 1000 W pulsed microwave irradiation.

TABLE 1

Selected Samples, microwave Power and Sample Temperature

| Sample | MW Power (1000 W full scale) | Sample Temp/C. | MW Pulse |
|---|---|---|---|
| Octanol | 15% | 18.9 | 1 s on, 1 s off |
| Octanol | 15% | 3 | 1 s on, 1 s off |
| Octanol | 15% | 0 | 1 s on, 1 s off |
| Octanol | 100% | 11.4 | 1 s on 1.5 s off |
| Octanol | 50% | −5 | 1 s on 1.5 s off |
| Hexane | 100% | −15 | 1 s on 1.5 s off |
| $10^{-4}$ M $H_2O_2$ in water | 100% | 11.5 | 1 s on 1.5 s of |
| $MgO_{(s)}$ light | 15% | 26.5 | 1 s on 1.5 s of |
| $MgO_{(s)}$ light | 100% | 27 | 1 s ramp up 10 s on 10 s off |

Figure 4:
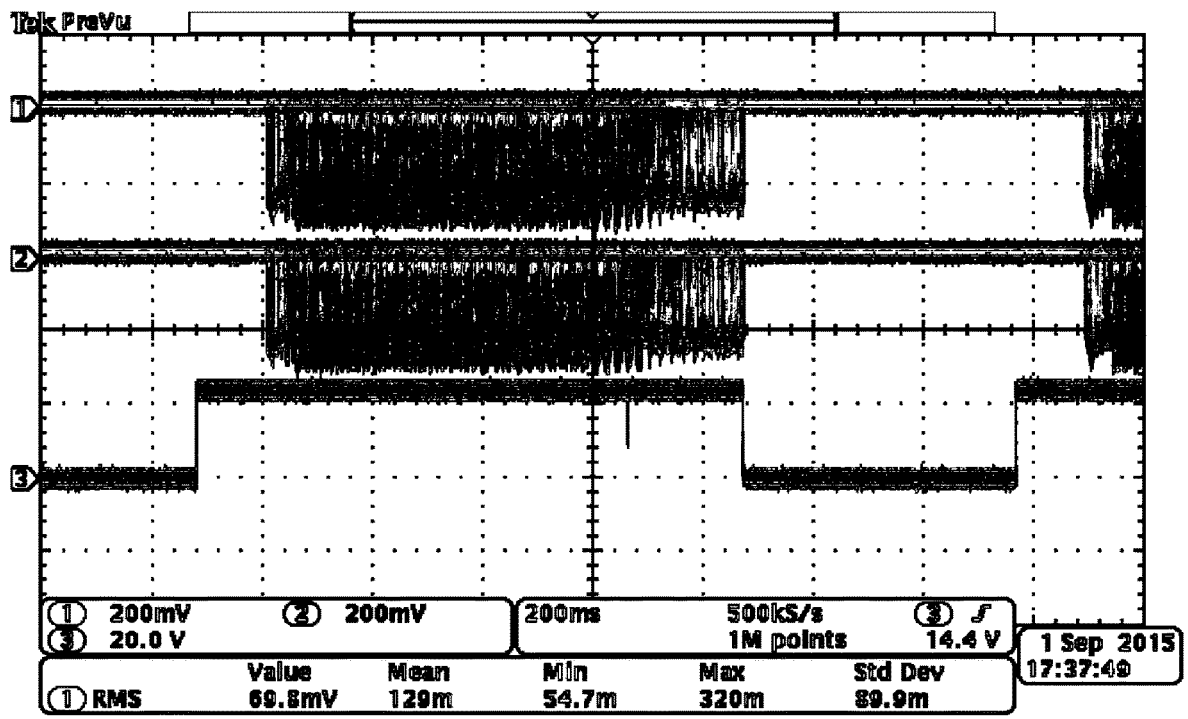
FIG. 4 is an example of an oscilloscope trace of microwave power as delivered 15\%.
Figure 5:
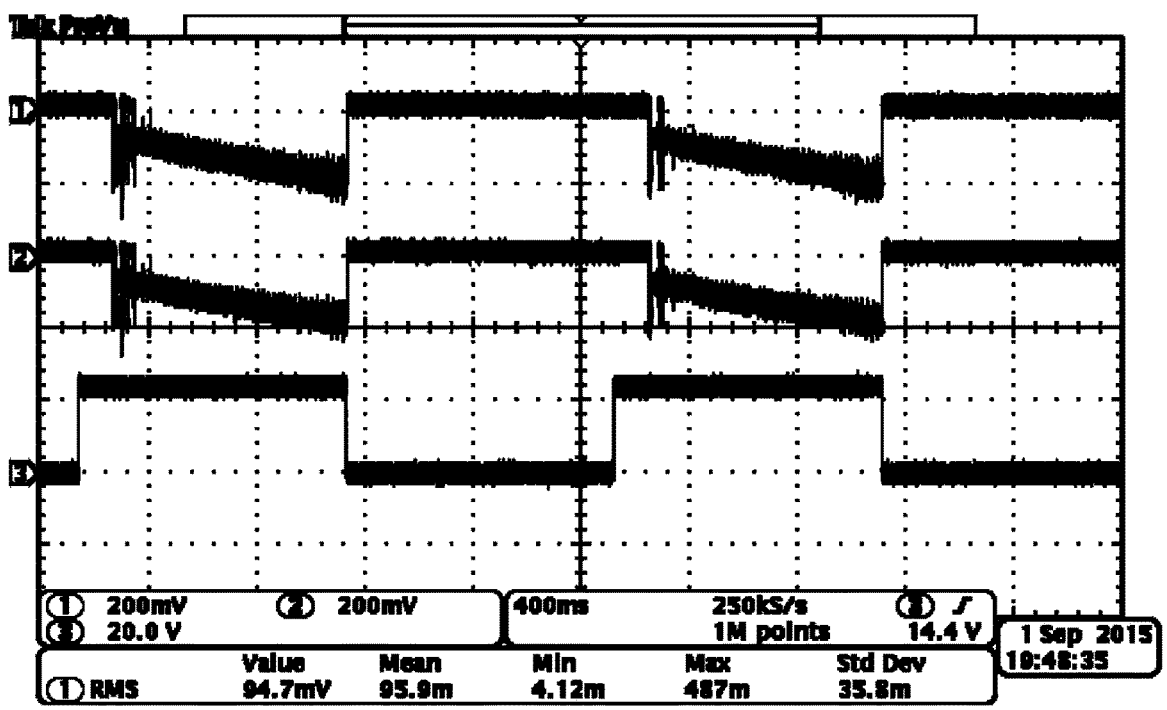
FIG. 5 is an example of an oscilloscope trace of microwave power at 100\%.

FIG. 4 illustrates an example of an oscilloscope trace of microwave power at 15%. The top, middle, and bottom traces are forward power, return power, and power on/off respectively. FIG. 5 illustrates an example of an oscilloscope trace of microwave power at 100%. The top, middle, and bottom traces are forward power, return power, and power on/off respectively.

Example 3. Simultaneous Irradiation of a Sample With Pulsed Microwave Irradiation and Nuon Beams (As an Ionizing Radiation) Probed In Situ Using Muon Spin Spectroscopy (μSR). Irradiation of Solid Magnesium Oxide (MgO) and Liquid Water ($H_2O$) Samples as Well as $H_2O$ in Water and Irradiation of Octanol In another example, the apparatus of FIG. 1 may be used to allow μSR experiments to take place while a sample is exposed to microwave irradiation in pulses of varying duty cycles. The use of ion beam irradiation and ionizing radiation is an essential component in radiation therapy, and is common in the food industry, material industry, and chemical industry. It is important to be able to tune the radiation effects. In this example, the radiation effects caused by an ionizing radiation are tuned with use of microwave pulses while keeping the temperature at a required preset temperature at different microwave powers up to 1000 W for an extended period and as low at almost 10 C. The ionizing radiation therapy is controlled using microwave pulses and the result is joint ionizing and microwave radiation therapy that work better than each therapy individually at any required temperature without causing burns to healthy tissues.

Figure 6:
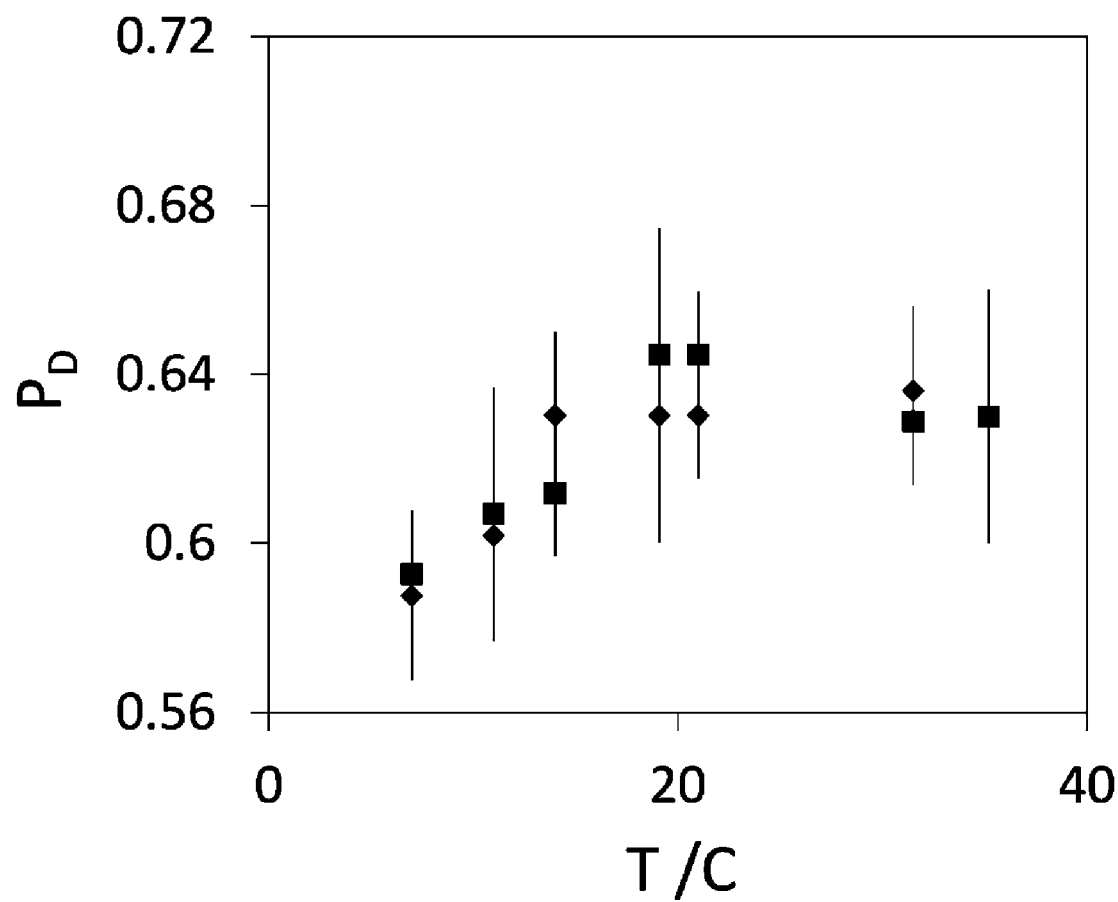
FIG. 6 is an example graph illustrating H2O diamagnetic polarization as a function of temperature.
Figure 7:
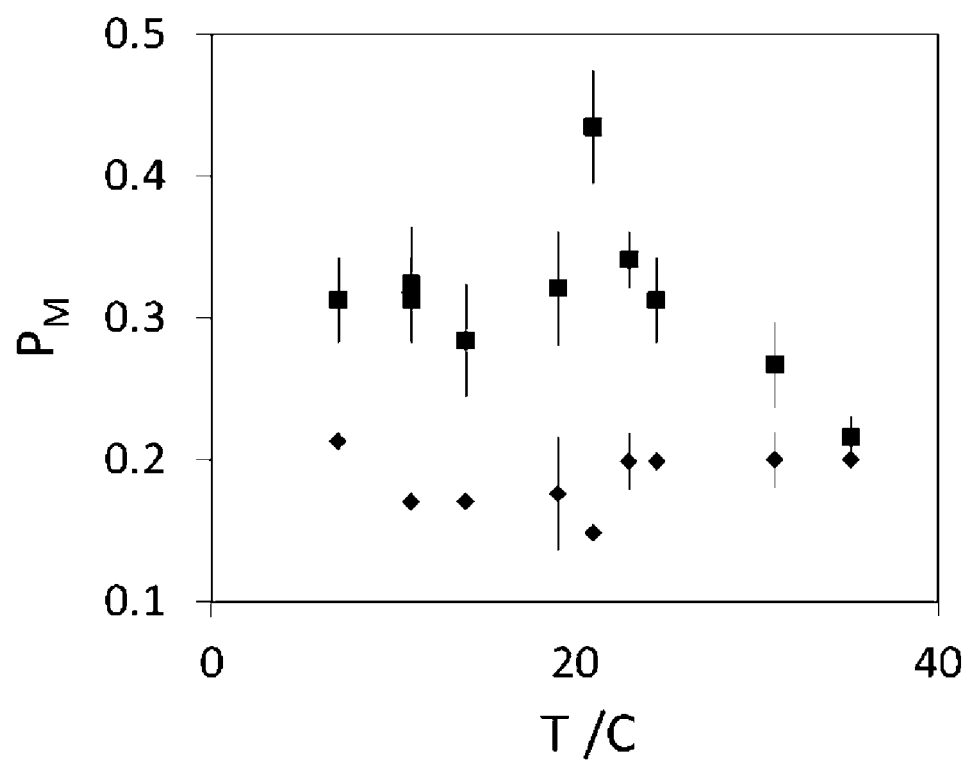
FIG. 7 is an exemplary graph of H2O Mu polarization as a function of temperature.

In one example, the pulse included power on for 1 s and off time of 1.5 s. This allows one to measure the sample in the presence and absence of microwave irradiation nearly simultaneously with minimal change in temperature (minimum change of temperature in power on and off was 0.1 C and maximum 2 C with full 1000 W applied to water). Of particular interest are the size of the asymmetry, which indicates the propensity of positive ions (muons in this case) to react with electrons to form atoms (Muonium in this case), and the relaxation, which indicates the reaction rate of muonium due to chemical processes. Most of radiation therapy and applications of ionizing radiations are via secondary electrons that generate free radicals that are reactive. As such the most important factors in radiation effects in radiation therapy and applications of ionizing radiation are electron positive ion combination and reactions of free radicals caused by irradiation. With microwave radiation it is possible to control both and this should be done at controlled temperatures with excellent temperature control since such NTMEs may vary at different temperatures. As an example, a plot of the polarization is shown in FIG. 6 and FIG. 7, which is directly proportional to asymmetry but corrects for signal measured from sources other than the sample itself. The most significant results may be obtained using samples of magnesium oxide and water. These results are discussed below. FIG. 6 is a plot of $H_2O$ diamagnetic polarization as a function of temperature with (squares) and without (diamonds) microwave radiation at 15% power. FIG. 7 is a plot of $H_2O$ Mu polarization (H surrogate produced in similar manner to proton electron combination) as a function of temperature with (squares) and without (diamonds) microwave radiation at 15% power.

MgO Results: In general, there are clear non-thermal effects on muonium formation. The results in MgO (a solid) and water (in liquid state) were opposite to each other. In MgO, the Mu formation was significantly inhibited by microwave radiation while in water the Mu formation was significantly increased. E.g. in MgO at 26.5 C the following may be observed:

$P_D$ under microwave off was 0.29+/−0.02. $P_D$ under microwave on (150 W) was 0.49+/−0.03.

$\lambda_D$ under microwave off was 0.003+/−0.0013/μs. $\lambda_D$ under microwave on (150 W) was 0.036+/−0.0016/μs.

$P_{Mu}$ under microwave off was 0.60+/−0.03. $P_{Mu}$ under microwave on (150 W) was 0.10+/−0.03.

This comparison suggest that microwaves can cause different radiation channels in solid and liquids to enhance and can control the ionizing radiation effects in the two differently. This provides different treatment modalities for solid vs. liquid based tumors and cancer cells in solid vs liquid environments. In addition, for materials chemistry applications in the solid state at certain temperatures the electron-hole recombination can be inhibited in the solid state while it could be enhanced in the liquids by microwave pulses.

Figure 8:
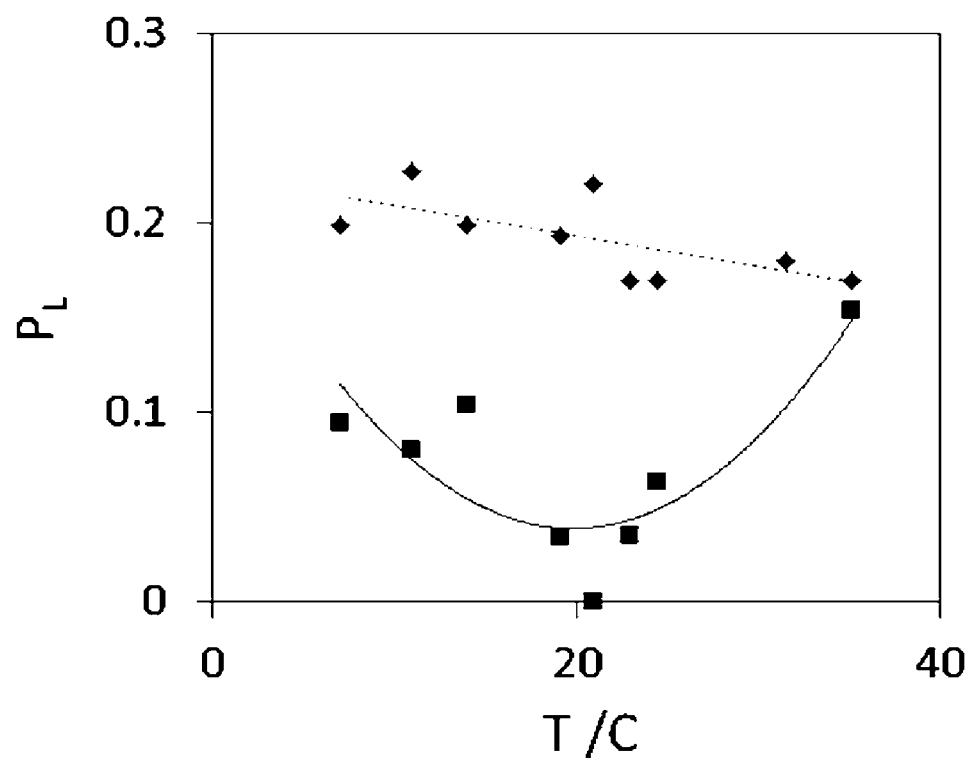
FIG. 8 is an exemplary graph of H2O loss fraction as a function of temperature.
Figure 9:
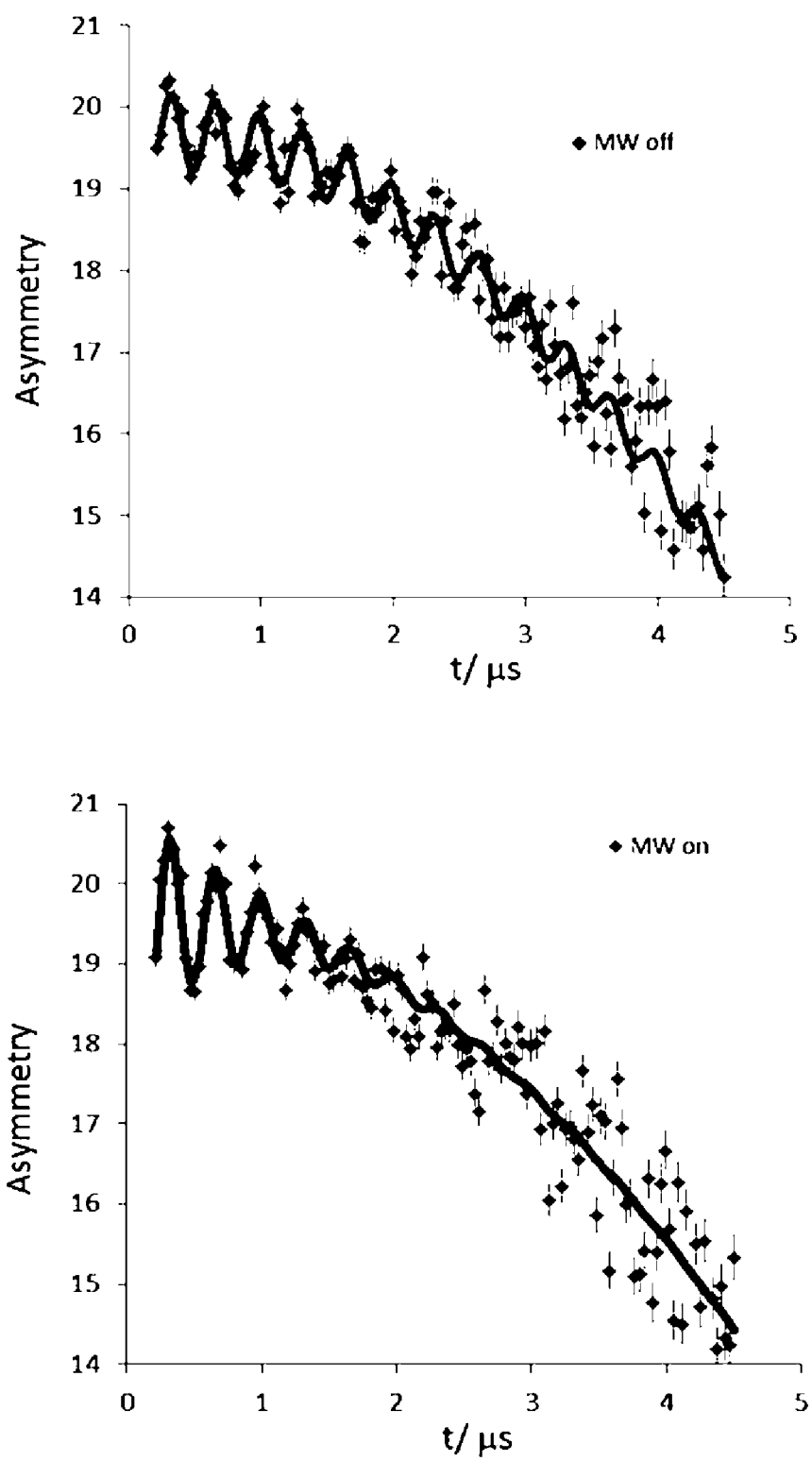
FIG. 9 is an exemplary graph of muonium asymmetry at 2 G in an H2O sample with and without microwave radiation at 15% power at 35.2 C

FIG. 8 illustrates $H_2O$ loss fraction as a function of temperature with (squares) and without (diamonds) microwave radiation at 15% power. FIG. 9 illustrates muonium asymmetry at 2 G in an $H_2O$ sample with (bottom) and without (top) microwave radiation at 15% power at 35.2 C.

Mu relaxation is also significantly larger in the absence of microwaves. Also from above results it is clear that $P_L$ (lost fraction) is significantly larger in the presence of microwave. The decrease of Mu fraction in the presence of microwave could be attributed to the separation of positive charges and electrons by microwave electric field. For the same reason the diamagnetic asymmetry is larger in the presence of microwave. The microwave could delay electron positive charged species recombination which could lead to a delayed Mu formation which can be the cause of increased lost fraction. These have implications on catalytic properties of solids under microwave. In general, this shows we can use microwaves to enhance solar cell efficiency and photocatalytic efficiencies.

H₂O Results

H₂O was measured at 15% power at three separate temperatures: 14 C, 21.2 C, and 35 C. The results are shown in FIGS. 6-9. A very significant increase is seen in both polarization and relaxation at 21 C, while the effect is much smaller at other temperatures. The decrease in the observed effect at higher temperatures may be due to the combination of a lower dielectric loss and higher dielectric constant at higher temperatures at the microwave frequency resulting in lower microwave penetration into the sample at these temperatures.

In summary, the data shows significant non-thermal microwave effects though the change in the relaxation and polarization of muonium, demonstrating the ability of non-thermal microwave (NTME) effects to play a significant role on radiation effects by influencing the rate, and nature of the chemical reaction. For example, in solid MgO the rate of muonium formation is reduced under microwave irradiation, while in water the rate is significantly increased suggesting that interfacing NTME with radiation therapies, can enhance their effectiveness by changing the radiation chemistry within the target sample. Conversely in semiconductor applications and other solid-state applications, such effects might also be used to shield or enhance radiation interactions with electronics, materials and devices resulting in new advanced materials and devices capable of novel or significantly enhanced functionality.

Example 4. Software of the Microwave Apparatus

Figure 10:
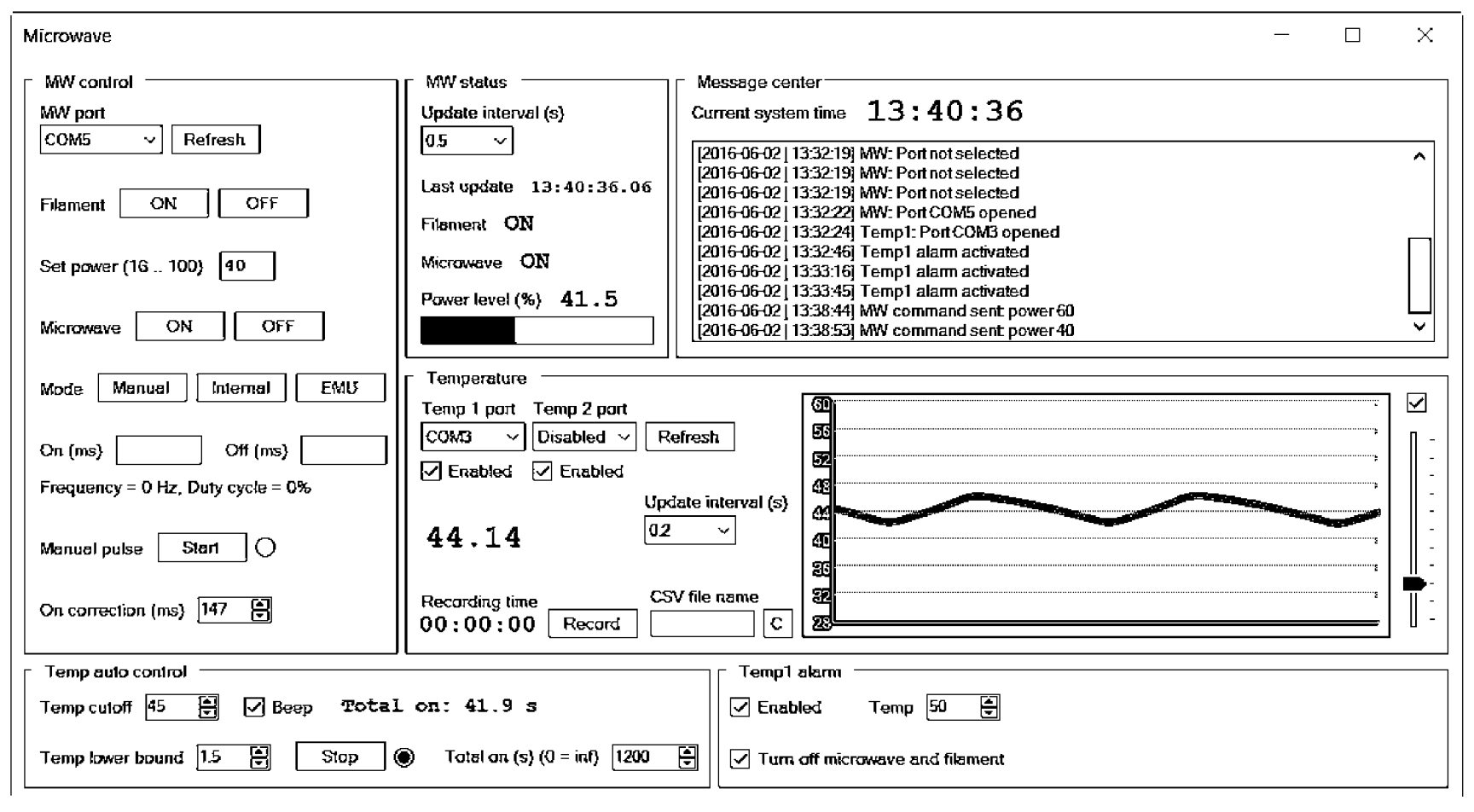

In one example, the software interface controlling the microwave apparatus, pulse duration, temperature monitoring and other functions may be written in C# and have a GUI interface. The main features are listed below, and a screenshot of the software GUI interface is shown in FIG. 10.

1) Hardware Interface

The software connects to the microwave controller circuit universal asynchronous receiver-transmitter (UART) interface via USB. The controller circuit is shown in FIG. 3, with relevant components of the circuit labelled in the figure.

2) Controlling the Magnetron Head

Three sets of commands can be directly sent in order to control the magnetron head. These command include turning on/off the filament, setting microwave output power, and turning on/off the magnetron. Turning on the filament is required for generating microwaves; therefore, it needs to be activated at least a few seconds before sending magnetron signals. The output power can be set in the range of 16% to 100% for a total output power of 1000 W. Sending on or off magnetron signals starts or stops microwaves generation, allowing the user to send controlled pulses of microwave radiation, with varying time intervals.

3) Continuous and Pulsed Mode

Figure 11:
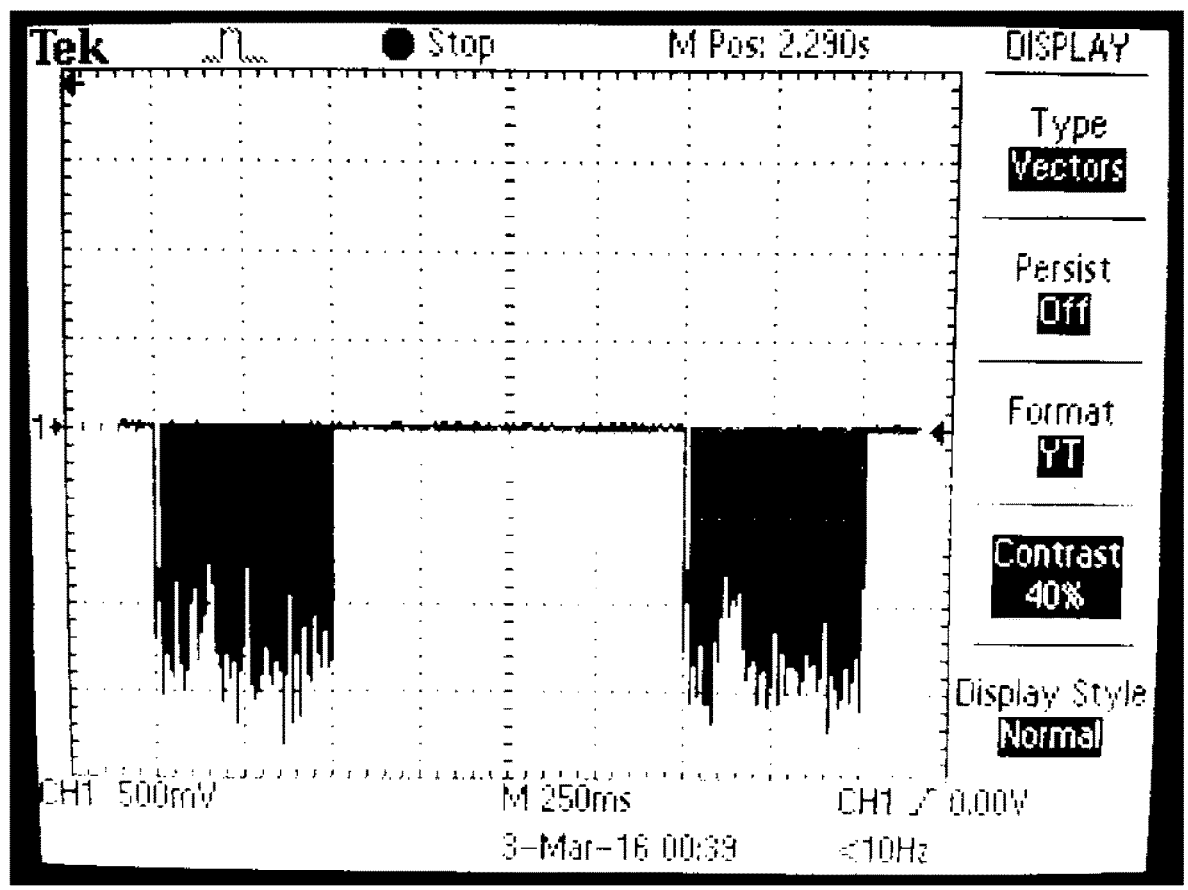
FIG. 11 is an example of a pulsed mode microwave waveform as measured by oscilloscope for 500 ms on and 1000 ms off pulses

Microwave system can operate in two different modes: continuous mode and pulsed mode. In continuous mode, the magnetron is simply activated to generate continuous waves regardless of measuring the temperature of the sample inside the waveguide. There is a simple on/off switch button in the software to do the job. In continuous mode due to constant irradiating of the sample with microwaves, the sample usually reaches rapidly to high temperatures and even a robust cooling system cannot cool it down to very low temperatures. Due to this fact, a better solution is to use pulsed mode. In pulsed mode, the software sends on-and-off signals in a rectangular waveform to the magnetron head. The frequency and the duty cycle of these signals can be set in the software easily. A user can set the duration of on-and-off signals down to 10 milliseconds. For example, by setting the on-and-off duration to 800 ms and 1200 ms respectively, the magnetron head would generate microwave pulses with the frequency of 0.5 Hz and duty cycle of 40%. Regardless of operating in continuous mode or pulsed mode, the output power of the microwave can bet set in the software with the range of 16% to 100% of the maximum power which is equivalent to a range of 160 W to 1000 W. The generation of pulsed microwave signals as set by the user and sent by the software was validated using microwave detectors connected to an oscilloscope. An example oscilloscope trace of the microwave pulses is shown in FIG. 11.

4) Status

The status of microwave system including filament, magnetron, and power level is refreshed every 0.5 s or higher as determined by the user and software. These status details could be used for auto temperature controlling system, as well as monitoring the equipment operation (e.g. alarms, warning messages, safety interlock operation, water flow status, user input requests etc.).

5) Temperature Monitoring

Temperature measurements of the sample cell, during microwave operation within the waveguide, are conducting using a high-precision optical probe manufactured by "OSENSA Innovations", alternative microwave friendly temperature probes can also be used. These optical temperature probes use a USB interface to connect to the computer. The software reads and interpret the temperature signal data with intervals as low as 0.2 s, with up to two temperature probes being able to be connected and read simultaneously by the software.

6) Auto-Temperature-Control (ATC) Mode

Figure 12:
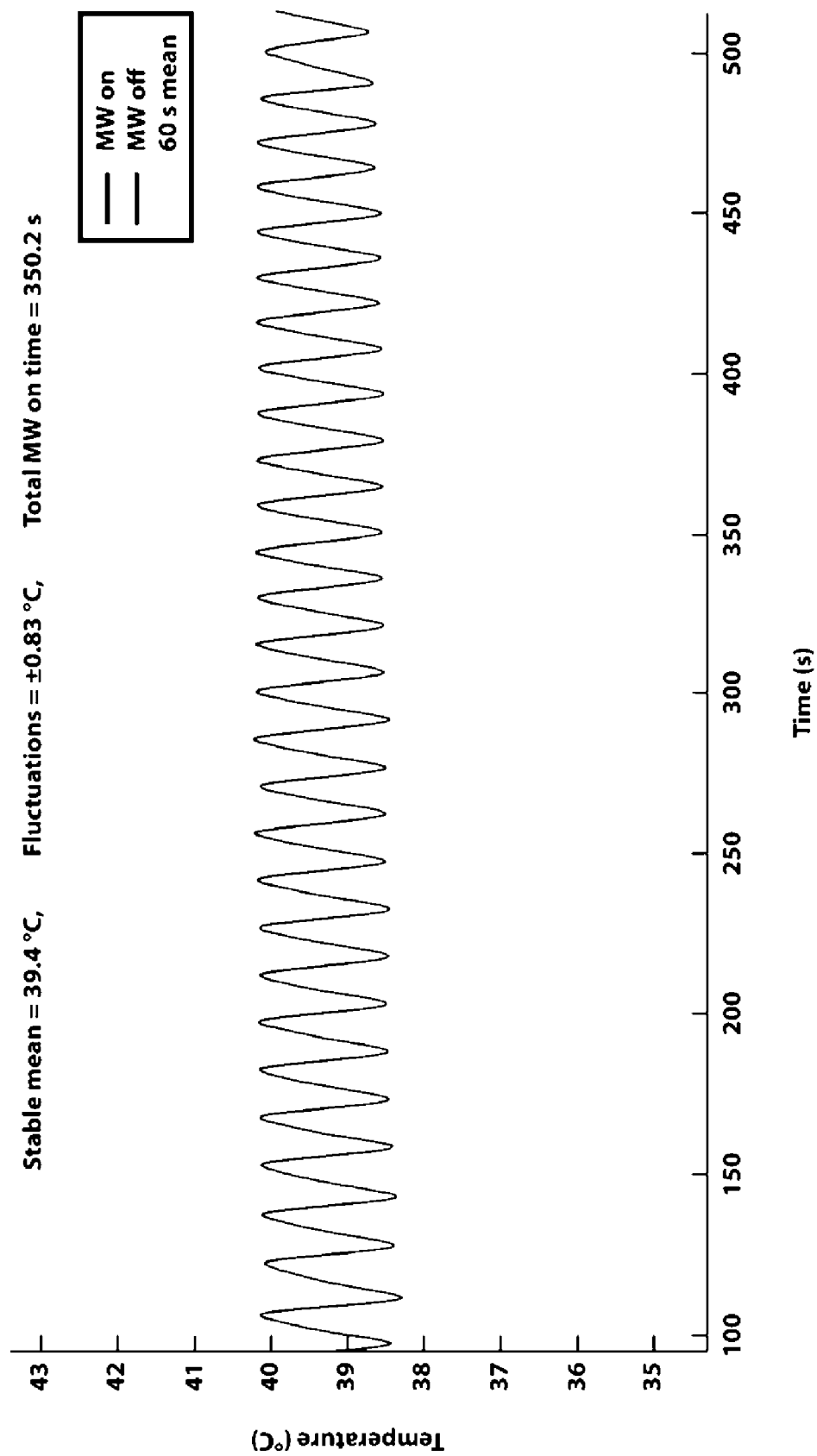
FIG. 12 is an exemplary graph of temperature fluctuations for a water-based sample.

As mentioned earlier in the previous section, the use of a pulsed mode is to prevent the sample to reaches very high temperatures and to let the sample cool down in each cycle. Even by just simply using pulsed mode with constant frequency and duty cycle, it is difficult to keep the temperature of the sample stable. Therefore, an additional well-designed mode called Auto-Temperature-Control (ATC) mode is to help the user by altering the frequency and the duty cycle of pulses regularly to keep the temperature at a certain level. In ATC mode, one can irradiate samples at a desirable constant temperature with low fluctuations. The fluctuations vary from sample to sample. As a general example, these fluctuations in a water-based solution are usually as low as ±1° C. (See FIG. 12 which illustrates temperature fluctuations for a water-based sample.). A high-precision optical thermometer is inserted inside the reaction chamber to measure the real-time temperature with interval as low as 0.2 s and accuracy of ±0.1° C. The software reads the temperature values and generates microwave pulses accordingly. The user can set two values for temperature: T and ΔT. T determines the desirable stable temperature and ΔT determines the allowable fluctuation in temperature from the set temperature (T). Here microwaves will be generated until the sample temperature reaches T and are then turned off until the temperature drops by no more than ΔT, whereupon the procedure will be repeated continually to keep the temperature at a certain range. The total duration in which the microwave pulse is on, can also be set, so after a predetermined total duration of irradiation, the system will be shut down.

7) Flow Monitoring

The flow rate of the circulation system which is used to decrease the temperature of the sample (in addition to tuning the duty cycle and pulse structure) is monitored by a Hall Effect flow sensor, which is tied in via hardware interface to connect with the microwave software allowing the software to ensure the sample is being cooled while under microwave irradiation.

8) Alarm

In case of any failure that results in an unexpected high temperature (higher than a predetermined critical temperature, failure of flow system etc.), the software is capable of flashing an alarm while electronically shutting down the entire microwave system.

9) Recording and Logging

Every command and every event monitored by the software is logged to a file in a human-readable format and is accessible easily without running the software. Temperature values also can be recorded to a separate file in CSV format.

Example 5. Using NTME's to Kill Pathogenic Bacteria in Samples While Maintaining a Constant Temperature In another example, the system of FIG. 1 may be used to test the non-thermal effects of microwave on bacteria. Two common pathogenic bacteria, E. Coli and S. Aureus, were irradiated under 2.45 GHz microwave under conditions detailed in table 2 shown below. The sample mean temperature was measured locally by using a high-precision optical thermometer.

TABLE 2

Detailed of some conditions used for bacteria experiments involving exposure to microwave irradiation

| Condition | 1 | 2 | 3 | 4 | 5 |
|---|---|---|---|---|---|
| Bacteria | E. Coli | S. Aureus | E. Coli | E. Coli | S. Aureus |
| microwave Power | 1000 W | 1000 W | 800 W | 1000 W | 1000 W |
| Duration | 4.8 min | 5.3 min | 2.5 min | 5 min | 5 min |
| Mean Temperature | 28° C. | 45° C. | 3.5° C. | 28° C. | 28° C. |
| Method | Bulk | Bulk | Smear | Bulk | Bulk |
| Buffer Solution | TSB | TSB | NaCl 0.85% | NaCl 0.85% | NaCl 0.85% |

Two different methods for placing the bacteria inside the microwave cavity was used, bulk and smear. In the bulk method approx. 2 mL of bacterial broth was placed on a surface of reaction cell (about 4 cm2) whereas in the smear, a minimal amount of bacterial broth was smeared on the surface to form a thin layer. Bacterial broth was prepared by inoculating a minimal amount of either bacteria from frozen bacterial stock, into 10 ml of tryptic soy broth, and incubating broth at 37° C. for 24 hours. For maintaining the temperature of broth, microwave radiations were applied by pulse and the duration indicated in the table is the total duration of exposure to microwaves when pulse is on, by the bacterial sample. The pulses were on the order of seconds. Control experiments were performed in identical conditions concurrent with the microwave experiments, under identical conditions minus the microwave irradiation. E. coli was used as a common Gram-negative bacterium since it is possible that Gram-negative bacteria would be more susceptible to transformation under an applied electric field than Gram-positive bacteria due to the differences in the structure of the Gram-positive cell wall and the Gram-negative cell envelope. To further investigation of microwave effects on the Gram-positive bacteria and compare them to the Gram-negative bacteria, S. aureus as a common Gram-positive bacterium was used. Moreover, the outer membrane only exists in Gram-negative bacteria. This extra thin layer has some unique characteristics such as the presence of negatively-charged lipopolysaccharides (LPS).

Figure 13:
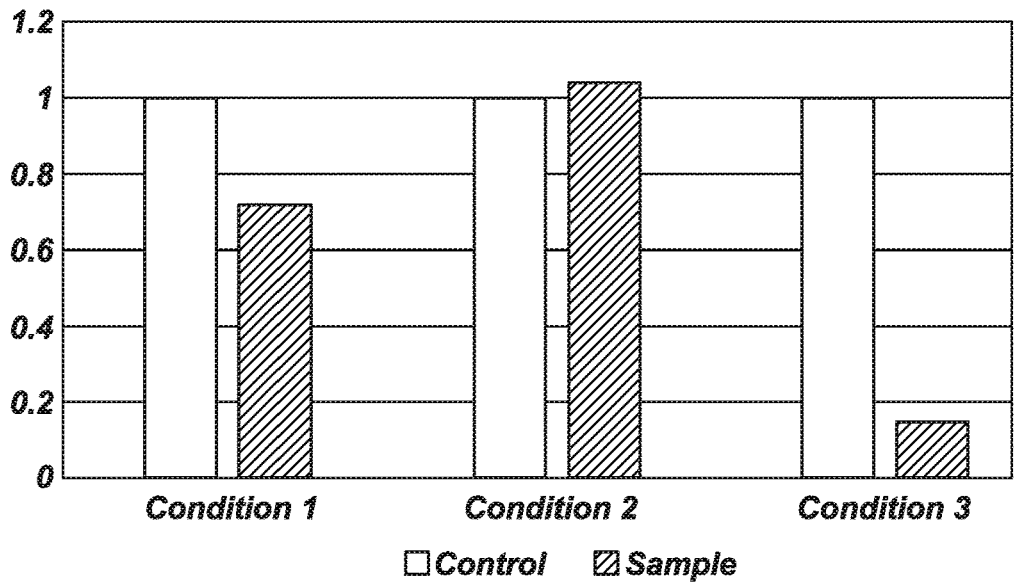
FIG. 13 is an example of the ratio of bacteria counts of a sample to control groups of *E. coli* and *S. Aureus*.
Figure 14:
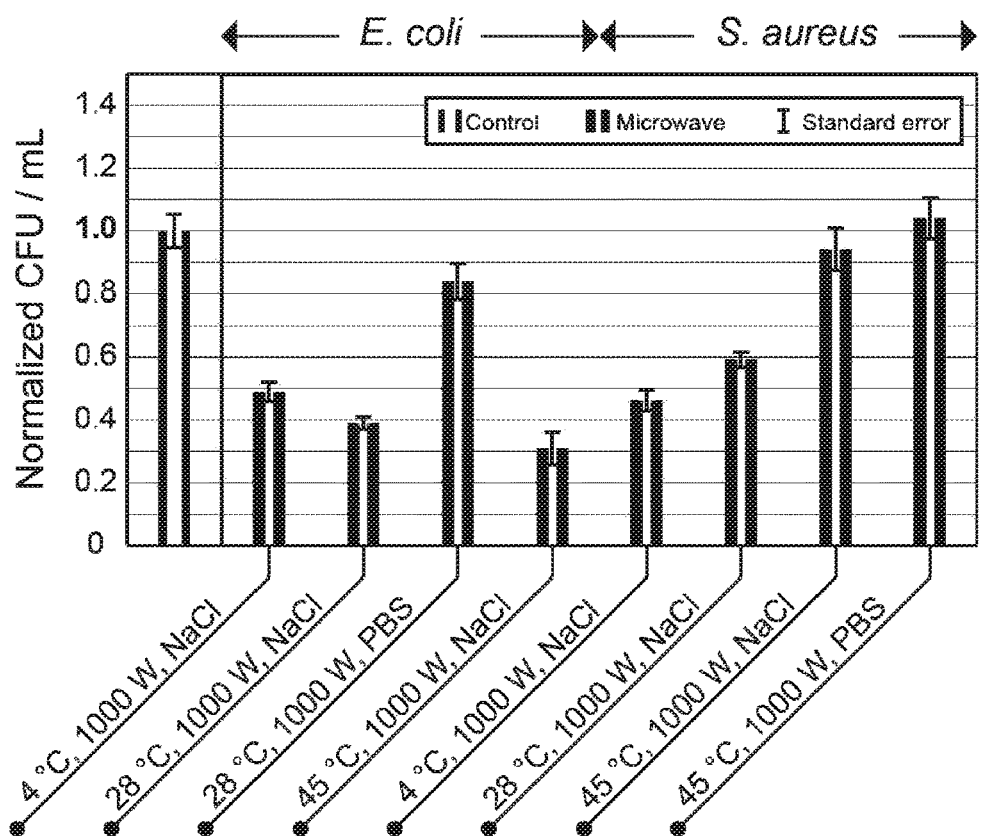
FIG. 14 is an example of a normalized colony forming unit count per milliliter of control and microwave irradiated samples for different parameters.

FIG. 13 demonstrates the ratio of sample group to control group sample group to control group for three conditions measured. The ratio of bacteria counts, of the sample to control groups of E. coli and S. Aureus, as per the experimental conditions defined by table 2. The sample group was exposed to MW radiation while the control group was not. FIG. 14 demonstrates the ratio of normalized colony forming unit count per milliliter of control and microwave irradiated samples for different experimental parameters tested. The single control error bar demonstrates the average error values for the both bacteria types. The bacterial samples were counted by plating the samples on Mueller-Hinton agar plates at various dilutions and the CFU determined after a 24 hr incubation at 37° C.

Example 6. Using NTMEs for Promoting Chemical Reactions

In another example using the embodiment of FIG. 1, a Fischer esterification reaction was used to study the effects of microwave radiations on kinetics of the reactions. A Fischer esterification reaction is a reaction between a carboxylic acid and an alcohol in the presence of an acid catalyst. Some esterification reactions occur naturally in wine during aging. By forming these esters, a range of aromas are introduced in wine and make it less acidic. The most important one is esterification of acetic acid with ethanol which yields ethyl acetate. This reaction is protonated catalytically by acetic acid itself and other tannins. Non-Thermal Microwave irradiation could thus be used to artificially age wine while removing some of the undesirable organoleptic side-effects of thermally heating wine.

In order to study the effect of microwave irradiating on esterification reactions, two alcohols including ethanol and methanol, and two acids including acetic acid and salicylic acid were used. For analyzing the products of the reactions, 1H-NMR spectroscopy was used and the solvent was CDCl3. Among multiple combinations of alcohols and acids, three of them was analyzed by using NMR both for control and sample solution. These reactions are detailed in Table 3 shown below.

TABLE 3

Esterification reactions details

| Reaction # | 1 | 2 | 3 |
|---|---|---|---|
| Acid | Salicylic Acid | Acetic Acid | Acetic Acid |
| Alcohol | Ethanol | Ethanol | Ethanol |

TABLE 3-continued

Esterification reactions details

| Reaction # | 1 | 2 | 3 |
|---|---|---|---|
| Catalyst | Sulfuric Acid | None | None |
| Molar Ratio (Acid:Alcohol) | 1:8 | 1:20 | 1:20 |
| Catalyst Concentration | 1% wt | 0 | 0 |
| Mean Temperature | 37° C. | 37° C. | 50° C. |
| microwave Power | 250 W | 500 W | 500 W |
| Duration | 300 sec | 400 sec | 400 sec |

The control solution was kept at the same temperature and at the same duration as sample solution but without microwave irradiating (using conventional heating only).

Figure 15:
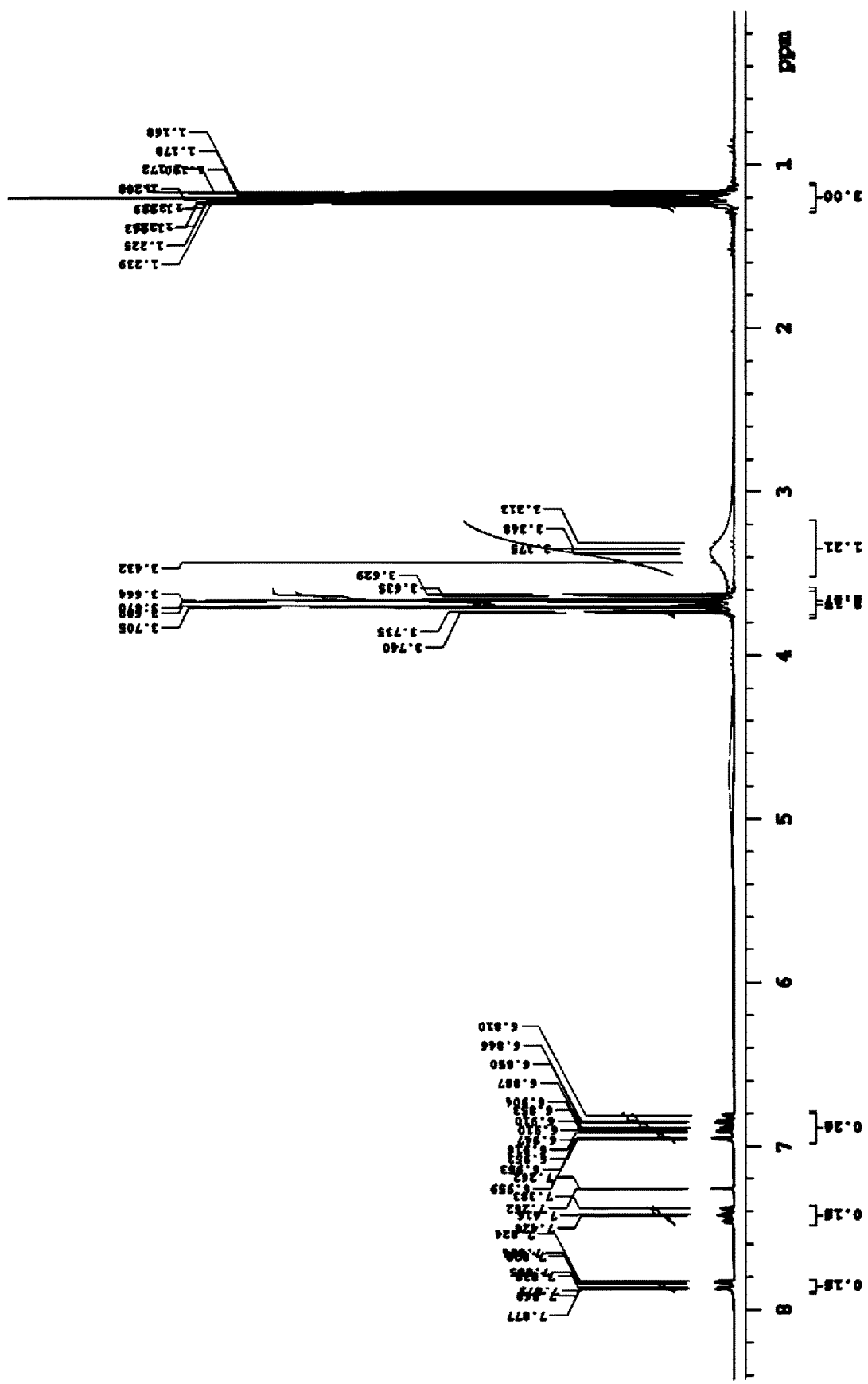
FIG. 15 is an example graph illustrating a comparison between a control and a sample.
Figure 16:
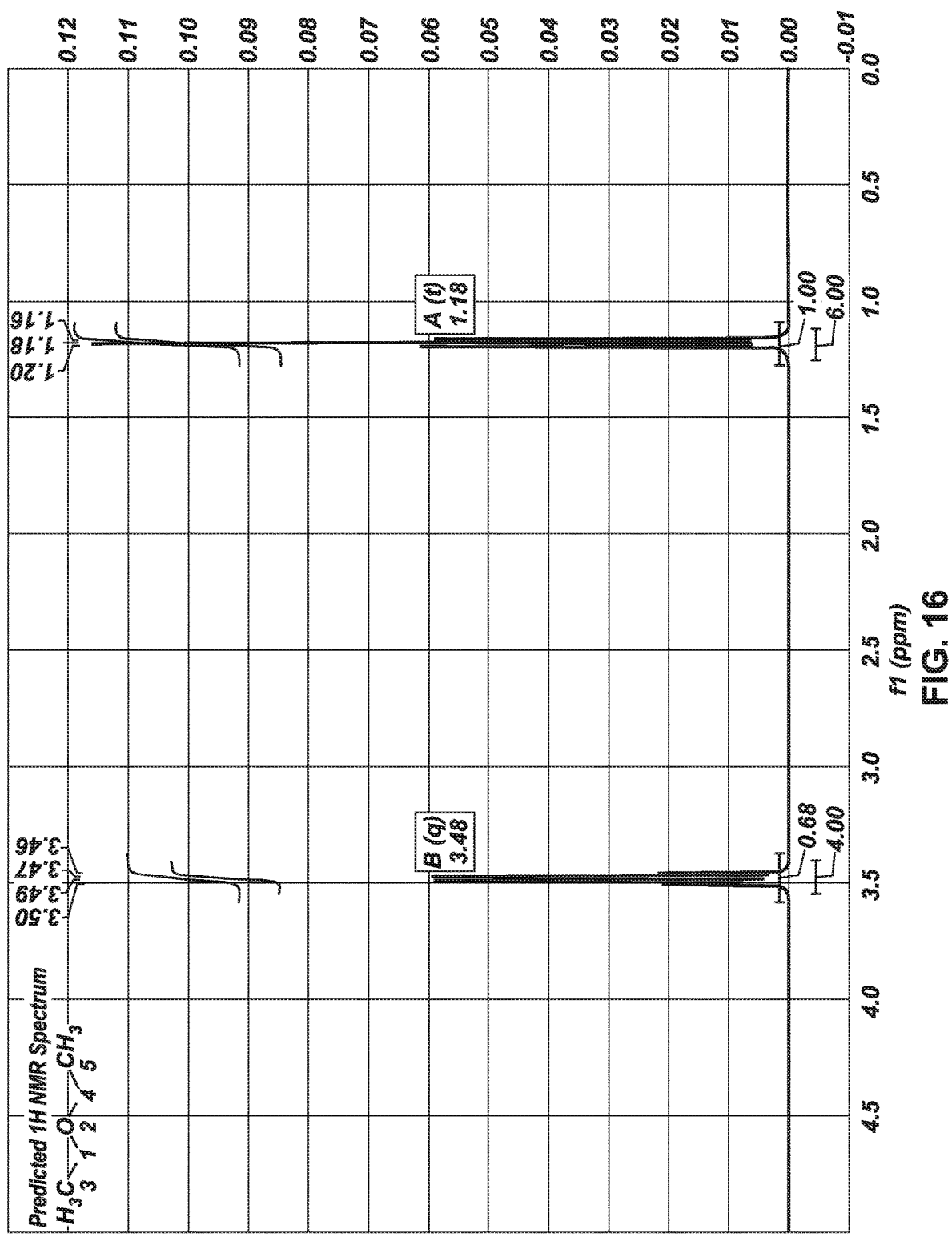
FIG. 16 is an example of calculated NMR spectrum for diethyl ether.
Figure 17:
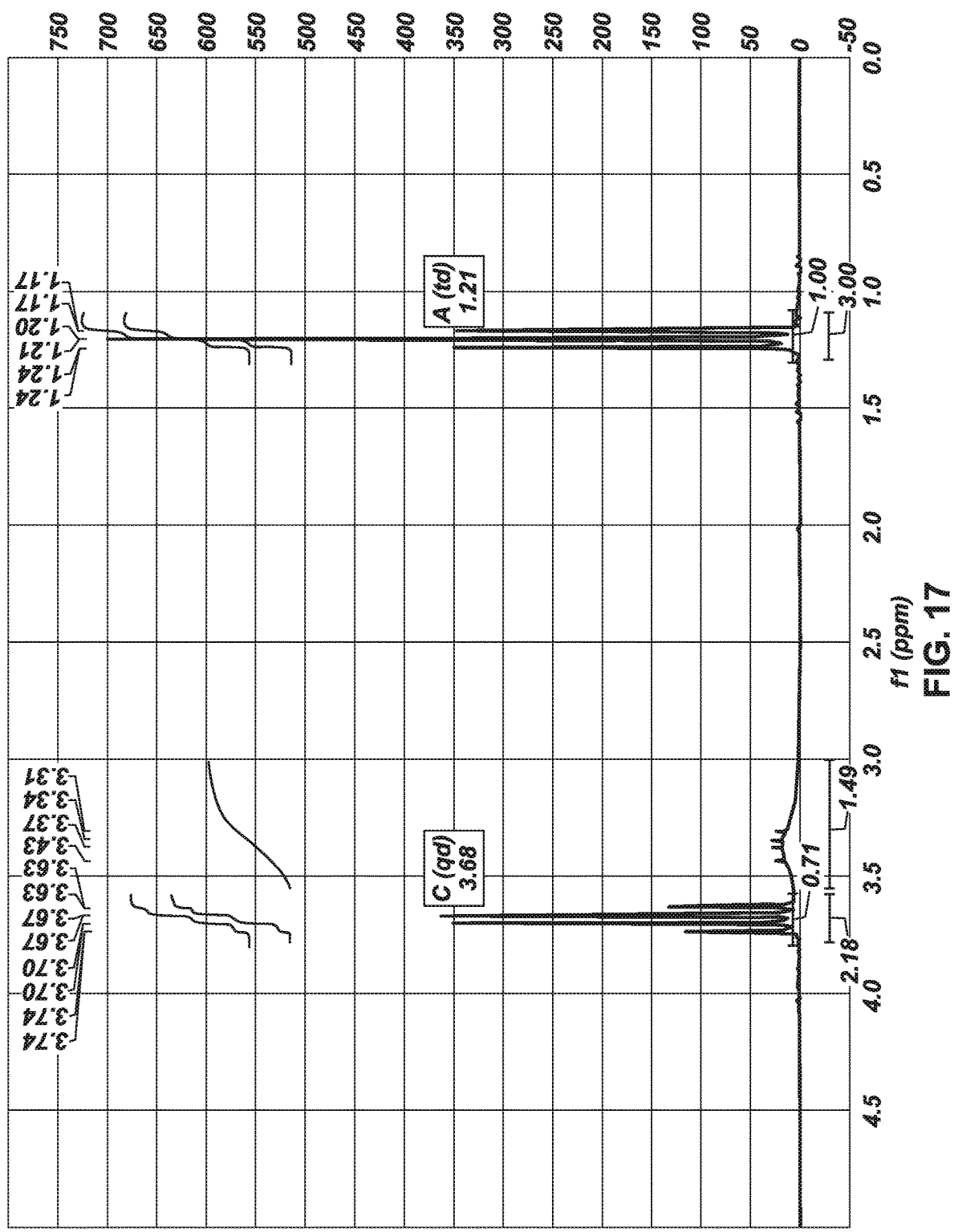
FIG. 17 is an example of NMR spectrum for the sample in reaction 1.
Figure 20A:
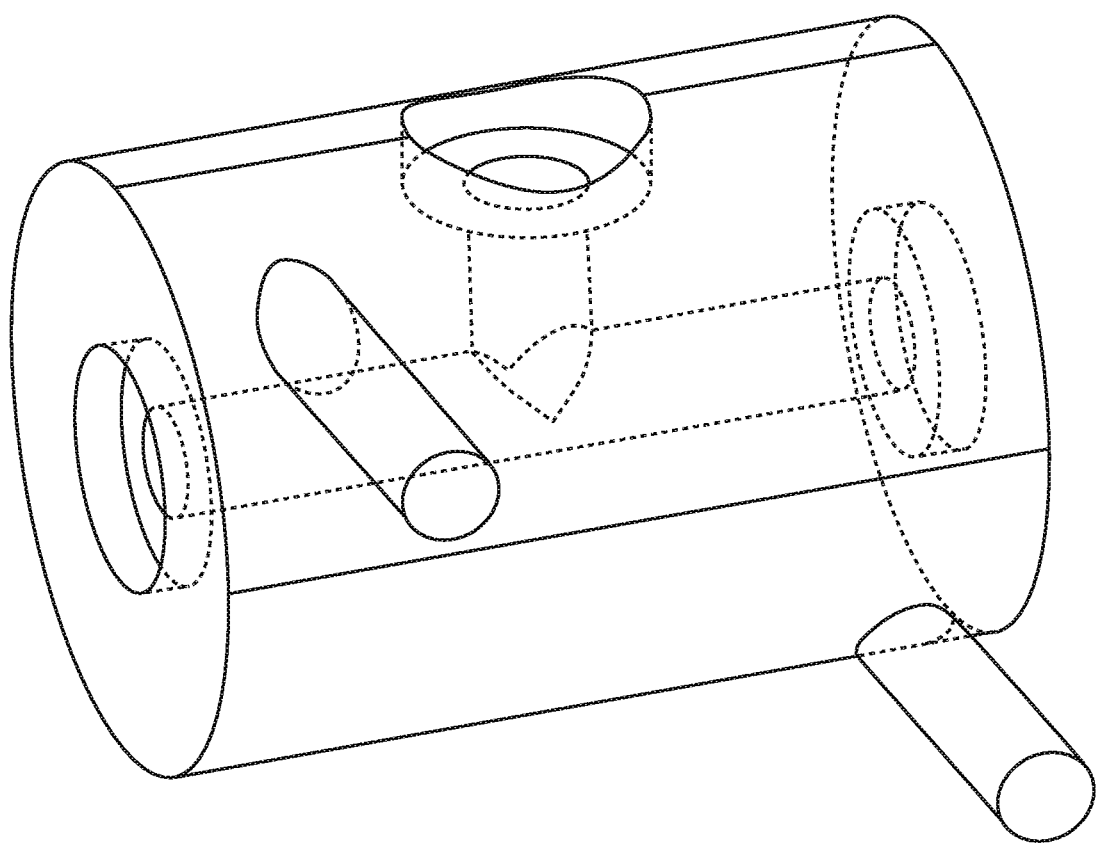
FIG. 20*a* is an exemplary design of a cell for in-situ spectroscopy and monitoring of a reaction.
Figure 20B:
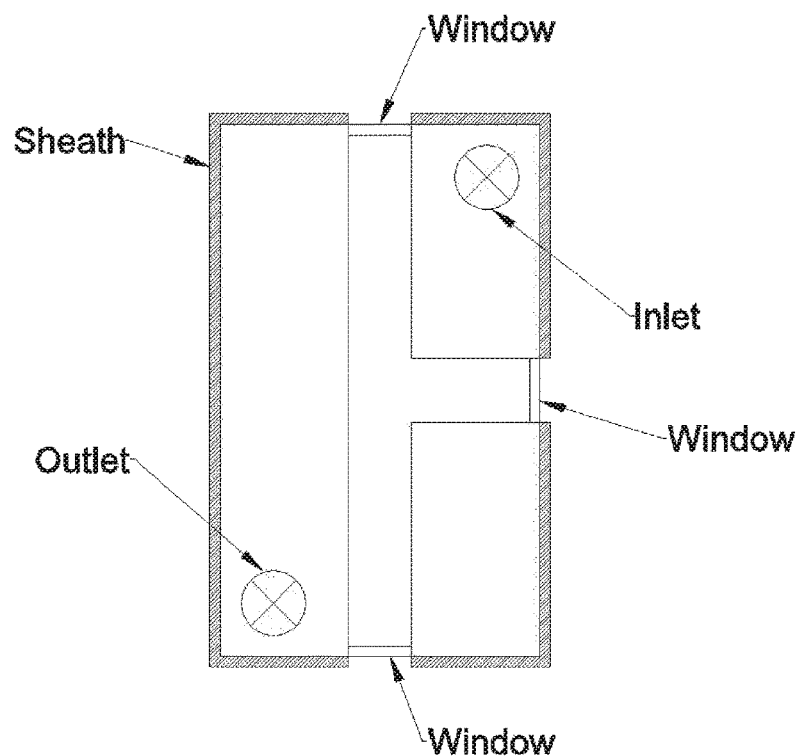
FIG. 20*b* is a side view of the exemplary cell of FIG. 20*a*.
Figure 20C:
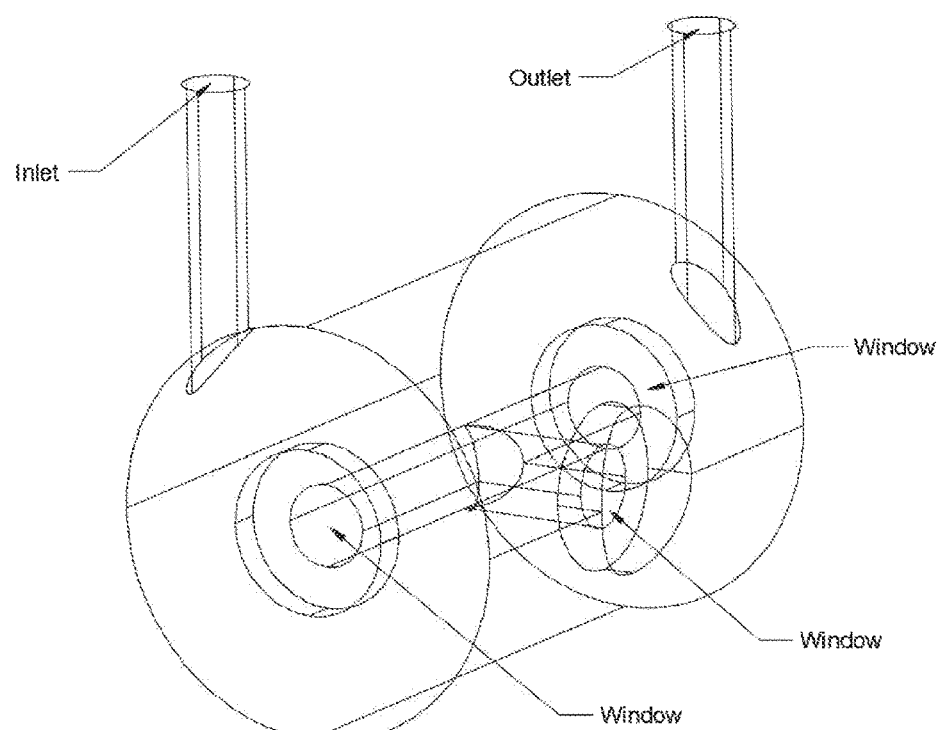
FIG. 20*c* is a perspective view of the exemplary cell of FIG. 20*a*.
Figure 21:
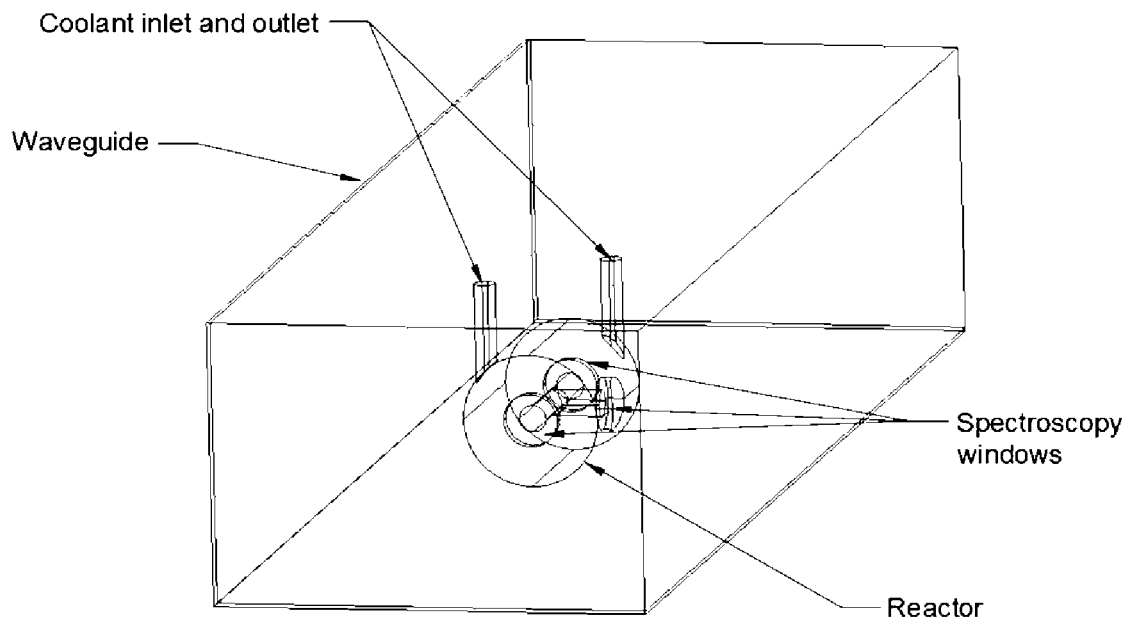
FIG. 21 is a diagrammatic view of the cell of FIG. 20*a* within a waveguide.

Analyzing the NMR spectra of reaction 1, as shown in FIG. 15 as an overlay of control and microwave irradiated samples, FIG. 16 as a calculated NMR spectrum of diethyl ether, FIG. 17 is the measured NMR spectrum, and FIGS. 20a-c as a relevant section of the sample NMR spectrum, we conclude that non-thermal microwave irradiation results in the formation of diethyl ether, through the acid-catalyzed condensation of ethanol. In an acid-catalyzed condensation of ethanol, partial dehydration with the formation of diethyl ether in presence of a strong acid (such as sulfuric acid in this reaction) occurs. The dissociated acid in aqueous environment produces hydronium ion H30+. A hydrogen ion protonates the electronegative oxygen atom of the ethanol and gives the ethanol molecule a positive charge. A nucleophilic oxygen atom of unprotonated ethanol displaces a water molecule from the protonated (electrophilic) ethanol molecule and produces water, hydrogen ion and diethyl ether. The reaction is displayed below in scheme one.

Scheme 1. Dehydration reaction of ethanol to form diethyl ether and water.

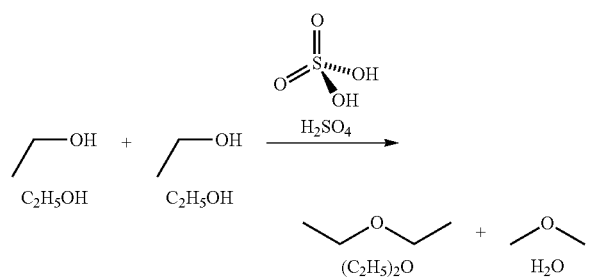

The evidence of occurring this reaction comes from the new peak that appears in the sample at 3.3 ppm. Diethyl ether has one large triplet peak at 1.2 ppm associated with the 6 CH3 protons, and one smaller quartet peak at 3.4 ppm associated with the 4 COC protons. The triplet peak overlaps with the ethanol peak but the quartet peak is clearly visible.

Figure 18:
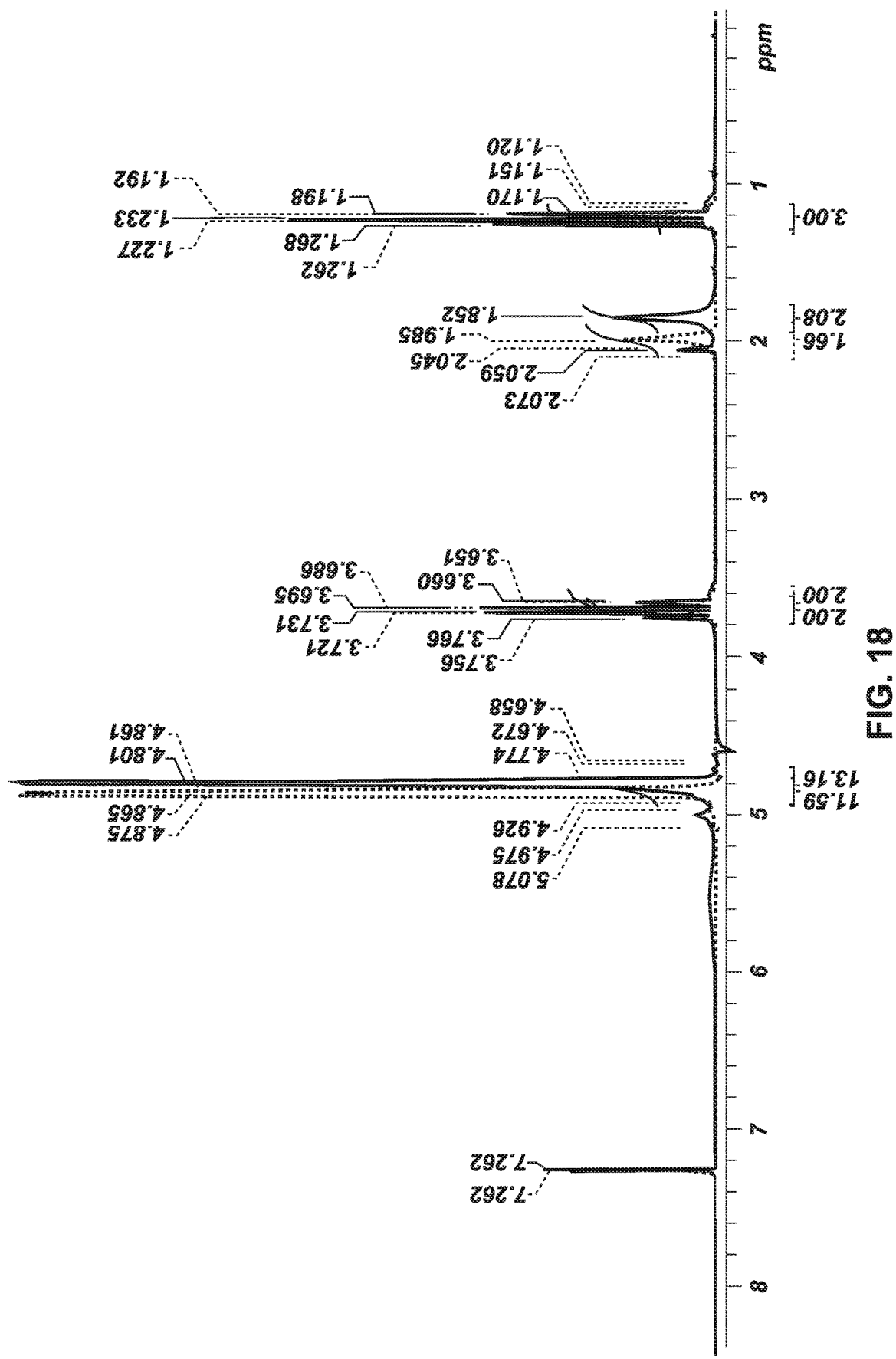
FIG. 18 is an example of Reaction 2: Comparison between Control (Gray) and Sample (Black)
Figure 19:
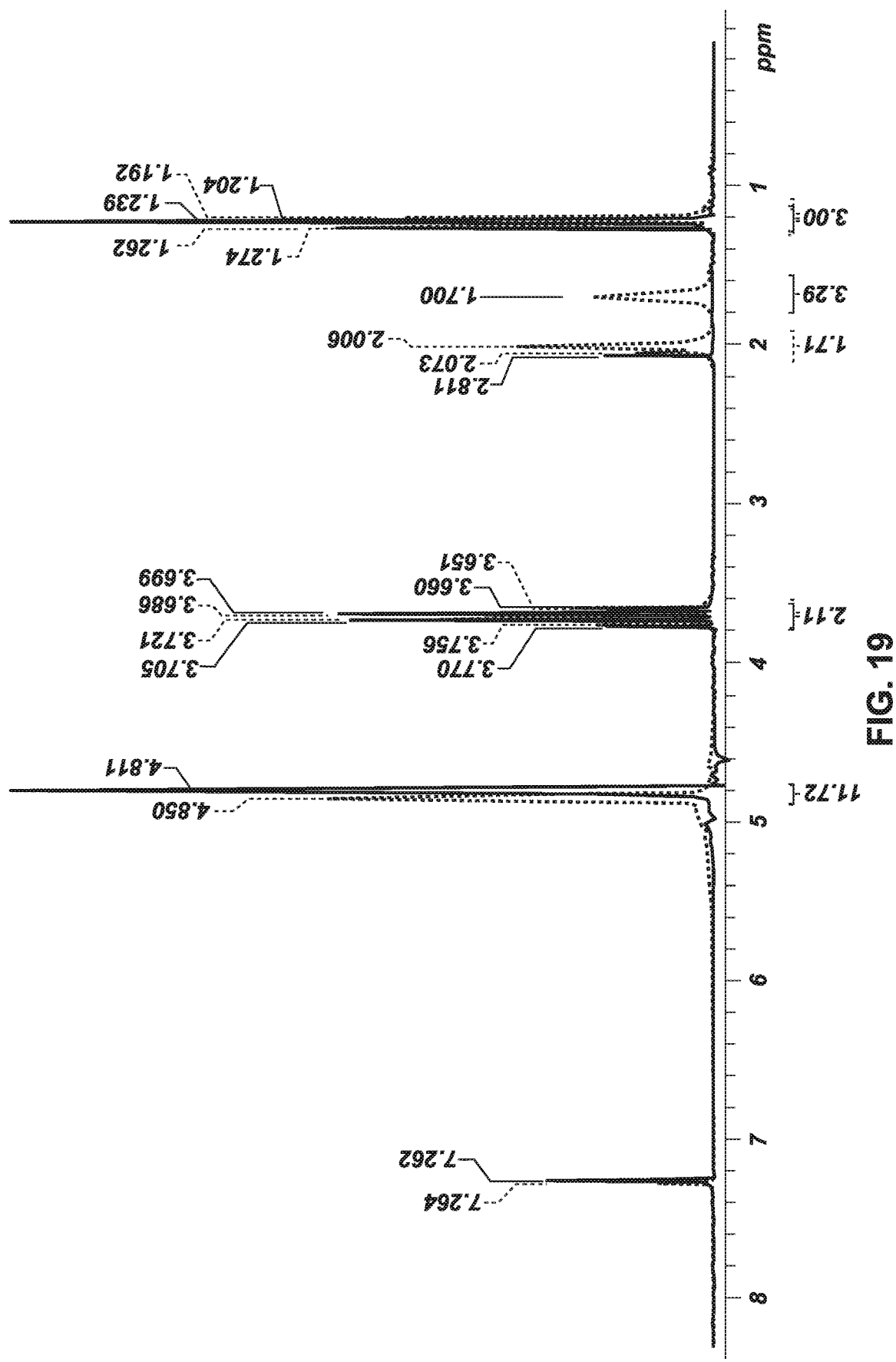
FIG. 19 Reaction 3: Comparison between Control (Gray) and Sample (Black)

Reactions 2 and 3 have the same reactants and conditions except the temperature and an overlay of the control and sample NMR spectra are displayed in FIGS. 18 and 19 respectively.

There is a very weak quartet peak for diethyl ether in both reactions 2 and 3, but it is too weak to be considered and is negligible. Therefore, basically no diethyl ether is formed for these two reactions, probably due to absence of sulfuric acid and low concentration of acetic acid.

The small peak around 2.05 ppm is related to CH3 group of acetic acid. We believe that acetic acid is completely converted to ethyl acetate, because the CH3 peak of ethyl acetate is lower ppm shift than that of acetic acid, explaining the emergence of the new peak around 1.7 ppm seen in the sample NMR, but not in the control group NMR.

The NTME effects observed through the synthesis of diethyl ether and ethyl acetate, demonstrate the ability of this invention to utilize NTME's for artificial wine aging where NTME's can enhance the favorable organoleptic properties of wine, while preventing heat related undesirable organoleptic properties from developing due to thermal microwave heating. In combination with the killing of pathogenic bacteria in example 5, they can be used in food and beverage processing, to enhance shelf-life, prevent microbial contamination and improve the organoleptic properties of said foods and beverages, as the processing temperature using NTME's is usually room temperature or below.

Example 7. Using Spectroscopy to Study In-Situ Chemical Reactions Under Microwave Irradiation In another example, a slight modification to the cell and the waveguide design of the embodiment of FIG. 1 allows for the inclusion of spectroscopically transparent ports, as shown by way of example in FIGS. 20a-c and FIG. 21, one can use the invention to study or irradiate samples simultaneously with microwave, optical (or other electromagnetic radiation) and if desired any ionizing radiation including muons. Here the sample cells are equipped with additional ports comprised of materials that are microwave transparent and are either transparent of have known transmittance properties in the desired spectroscopic range. For example, in the case of infra-red or UV-Visible spectroscopy the windows chosen need only be IR or UV-Visible transparent, or have known transparency properties that can be accounted for, and the electromagnetic radiation coupled to a fiber optic waveguide that can be used to deliver it to the optical window and collect the transmitted radiation for analysis from the other window. Similarly, other radiofrequency (RF), electromagnetic, or acoustic spectroscopies could be used to probe or alter the samples while under microwave irradiation, through use of appropriate sample windows and delivery media of the electromagnetic radiation.

Alternatively, the waveguide may also be modified, to allow for the addition of magnets and magnetic fields to surround the sample. As demonstrated by the use of the system in high magnetic fields during μSR spectroscopy, the placing of the system in a magnetic field, followed by RF pulses, can allow for the system to be modified to perform in-situ nuclear magnetic resonance (NMR) spectroscopy either simultaneously or in a pulsed manner alongside non-thermal microwave irradiation to probe, and characterize the chemical processes in the sample.

Given the ability to pulse microwaves into the system, similar to the earlier example with μSR spectroscopy, the microwave system can also be pulsed to allow binning of the spectroscopic and microscopic, and all other physicochemical properties data, through fast pulses of electromagnetic radiation during both the microwave ON and OFF states. This would enable improved signal to noise ratios over multiple scan events as well as an improved understanding of the system behavior under non-thermal microwave effects by simultaneously observing the system spectroscopically with and without microwave irradiation at nearly the same temperature and temperature profile during microwave off and microwave on with an average temperature error of less than 2 percent. This has not been available based on previous teachings. These online measurements serve as on line feedback to enhance the microwave applications in materials chemistry, chemical synthesis, industrial applications and radiation therapy, including all concurrent therapies, with one of the concurrent therapies being microwave therapy, by making maximum microwave effects on the target with minimal effects on the surroundings and therefore in the case of radiation therapy or microwave ablations it makes minimum collateral damage to the surrounding tissues.

Figure 22:
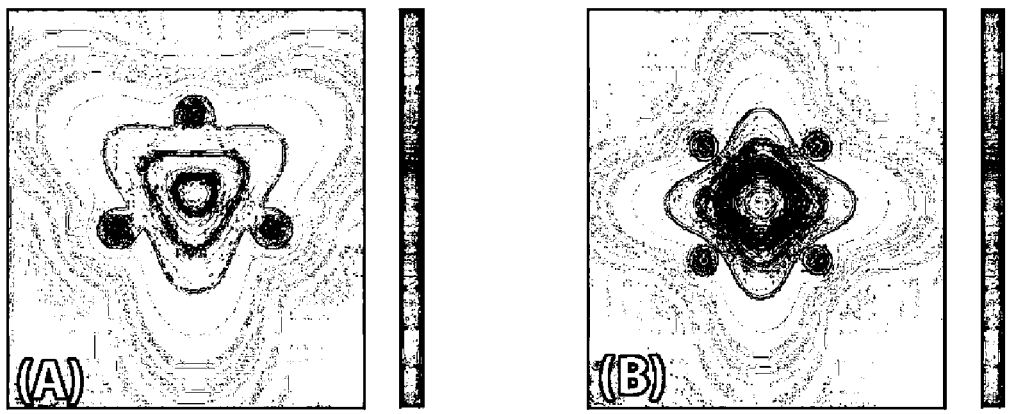
FIG. 22*a* is an example of a heating profile for an antenna array using three antennas.
FIG. 22*b* is an example of a heating profile for an antenna array using four antennas

In other embodiments, a method may exploit both thermal effects in controlled manner and NTME in medicine in order to ablate or damage cancerous tissue and tumor in human or animal body. One technique uses NTME and particularly the high frequency altering electric field of microwave to disable the cellular mechanism of target cells. An array of "n" monopole microwave antennas is used to generate microwaves. The electric field and the total energy at the center of array is improved by a factor of n and n2 respectively as shown in FIG. 22 which illustrates simulated heating profiles ($V^2/m^2$) of antenna arrays using (A) three and (B) four antennas. The heat generation rate at the center of the array is improved by a factor of (A) 9 and (B) 16 over a single antenna by using constructive antenna phasing.

Several techniques may be used to cool down the adjacent tissues. In one example, a Peltier device may be attached to a ceramic plate and placed in the inner area of antenna array. The outer area doesn't need to be cooled down due to low heat generation of those areas as shown by temperature profiles of FIG. 22.

Figure 23:
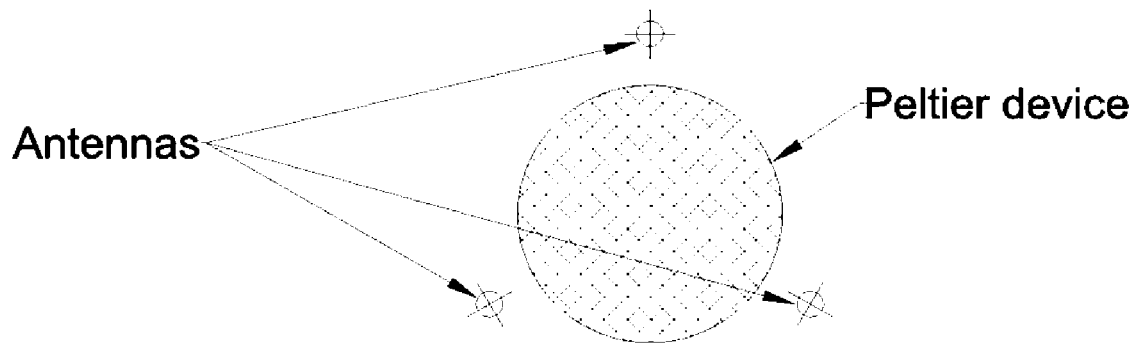
FIG. 23 is an example of an array of three antennas with a Peltier cooling device between the antennas.
Figure 24:
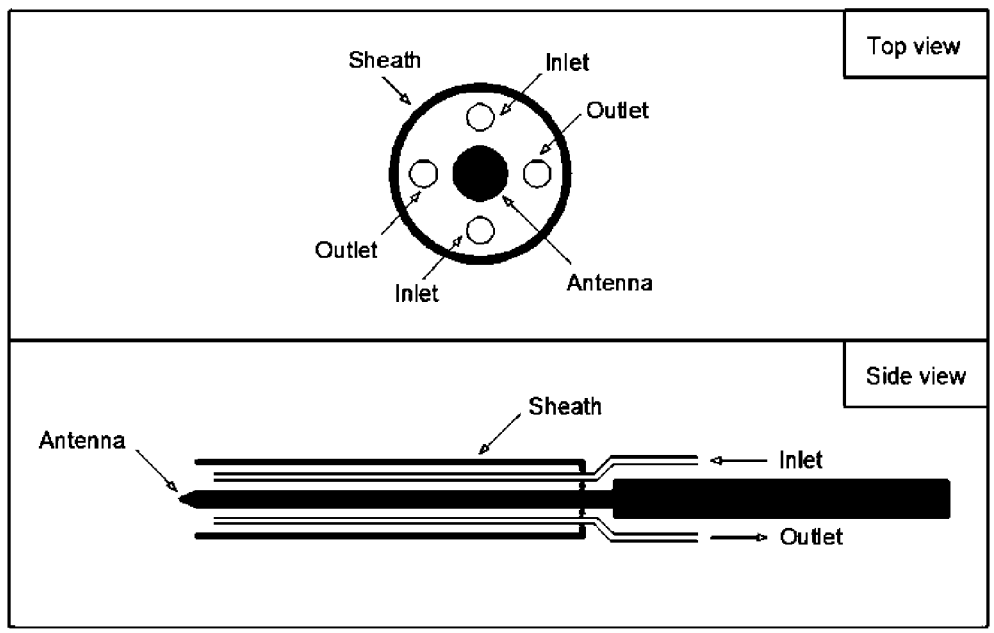
FIG. 24 is an example of a microwave surgery tool for laparoscopic and percutaneous surgeries.
Figure 25A:
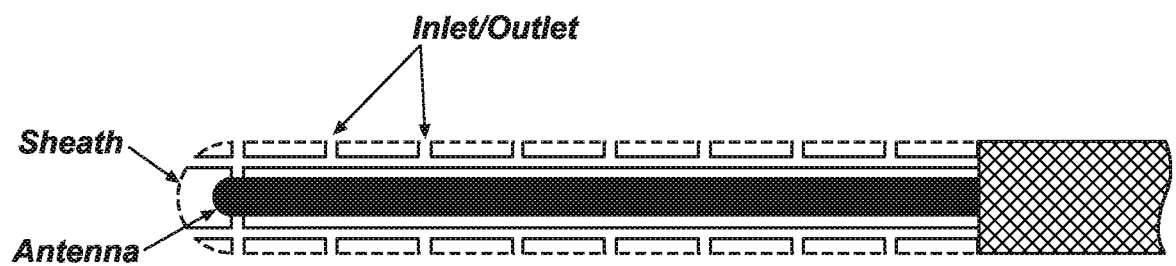
FIG. 25*a* is a side view of a microwave surgery tool
Figure 25B:
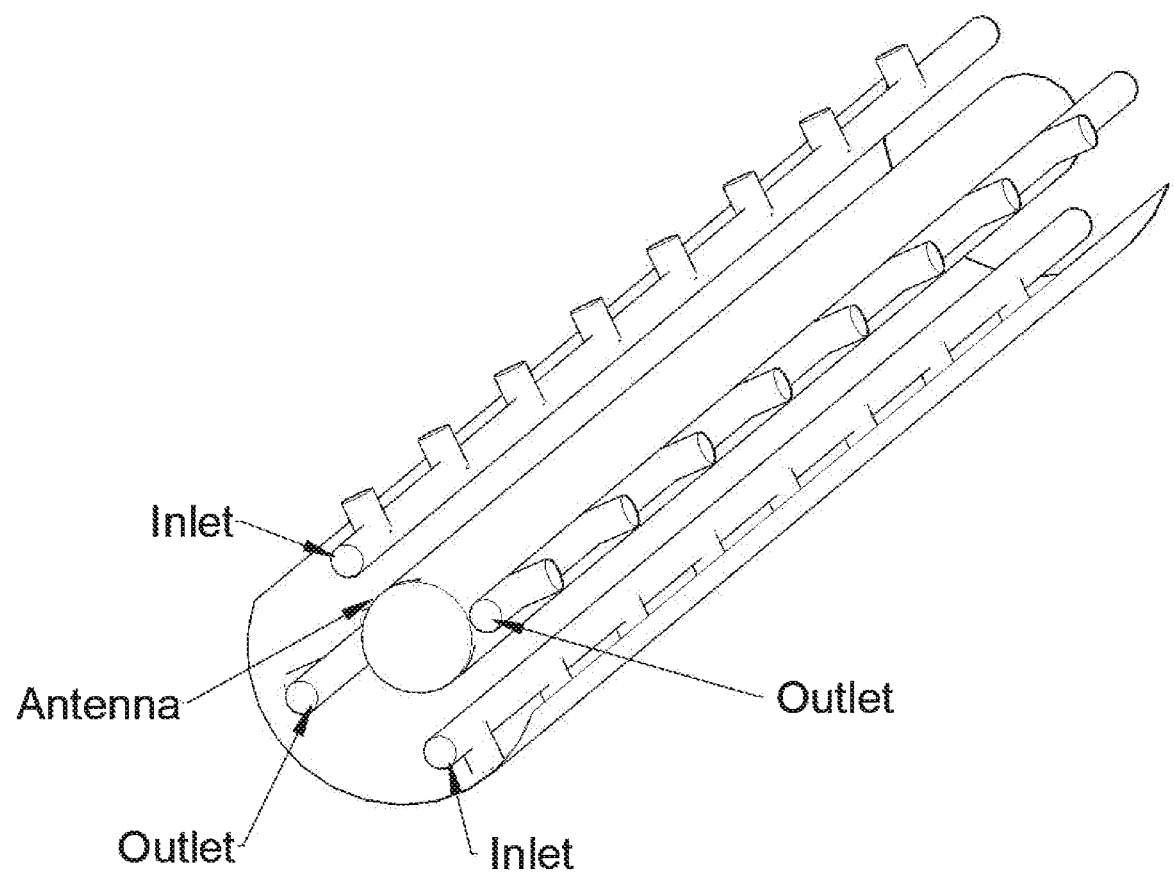
FIG. 25*b* is a perspective view of the tool of FIG. 25*a*.
Figure 26:
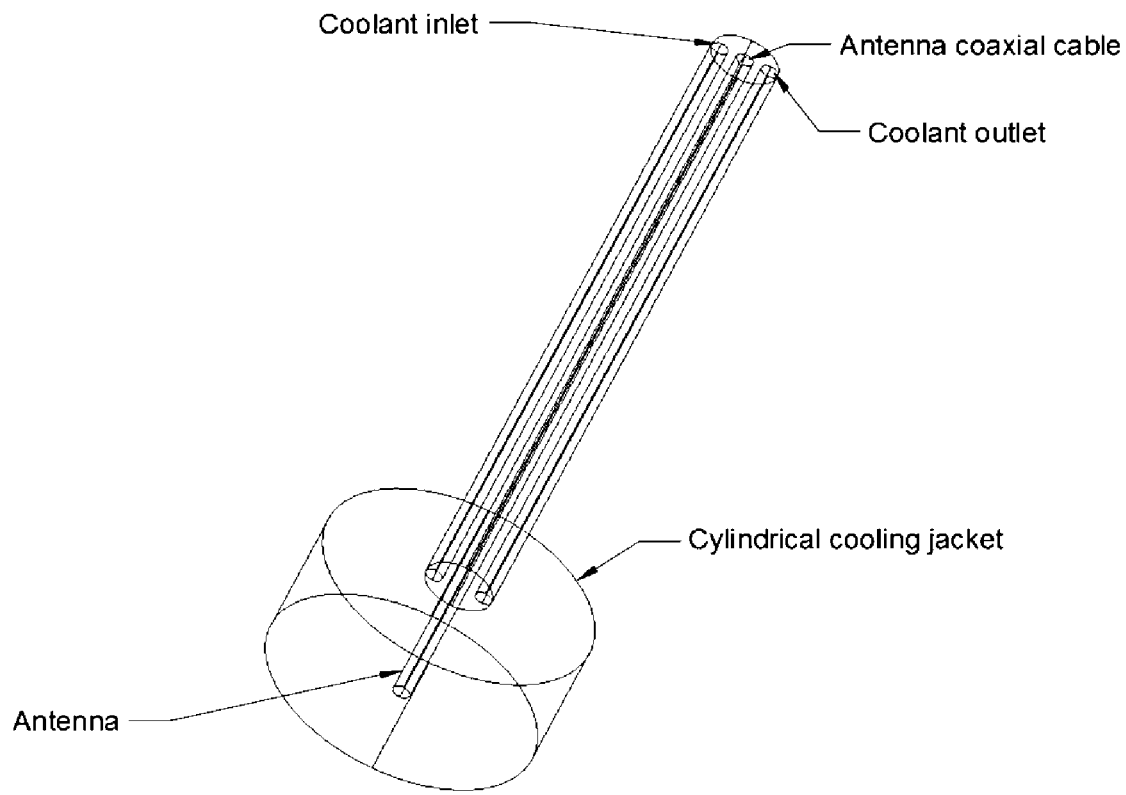
FIG. 26 is an example of a microwave therapy tool.

FIG. 23 illustrates an array of 3 antennas with a Peltier device in the middle. FIG. 24 illustrates a microwave surgery tool for laparoscopic and percutaneous surgeries comprising of a microwave antenna, an outer sheath and two or more inlet and outlet pipes for any air or liquid flow for cooling purposes. FIGS. 25a-b illustrate a flexible microwave surgery tool for treating different types of cancers such as but not limited to lung, tracheal or gastric malignancies (top: side view, bottom: 3D view). FIG. 26 illustrates a microwave therapy tool comprising of a microwave antenna in the middle and a cylindrical cooling jacket at the top with inlet and outlet to circulate cooling liquid.

Figure 27:
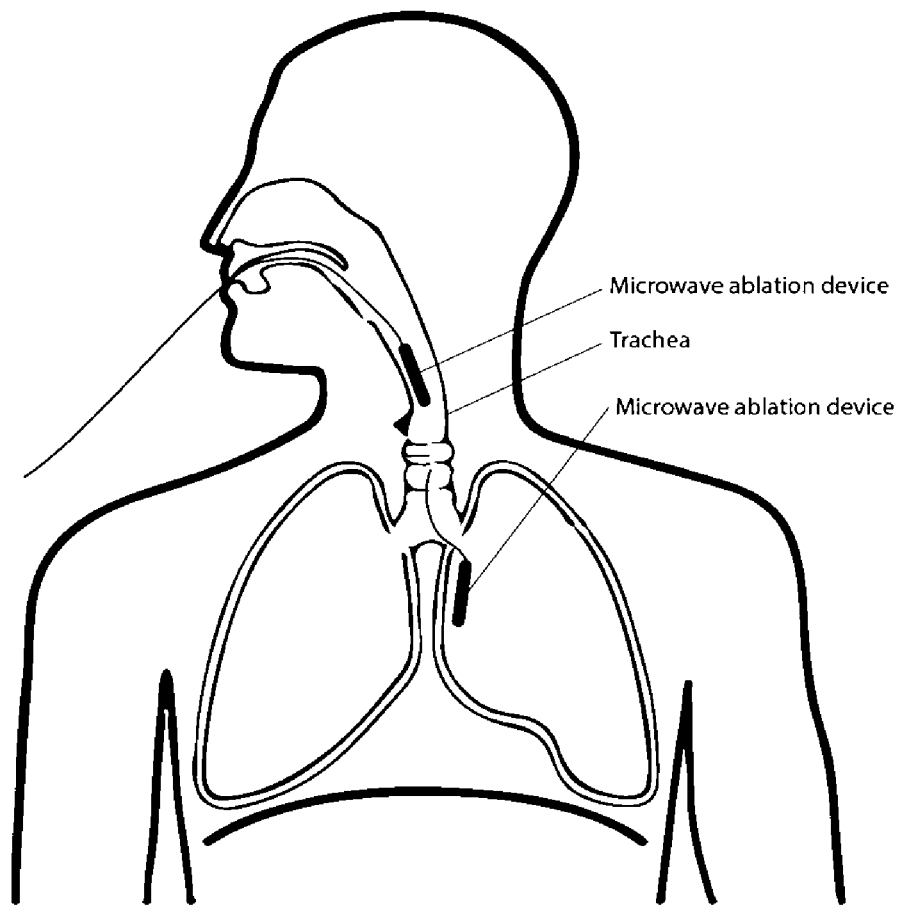
FIG. 27 is a diagram of an example microwave non-thermal ablation device as used for treating the respiratory tract.
Figure 28:
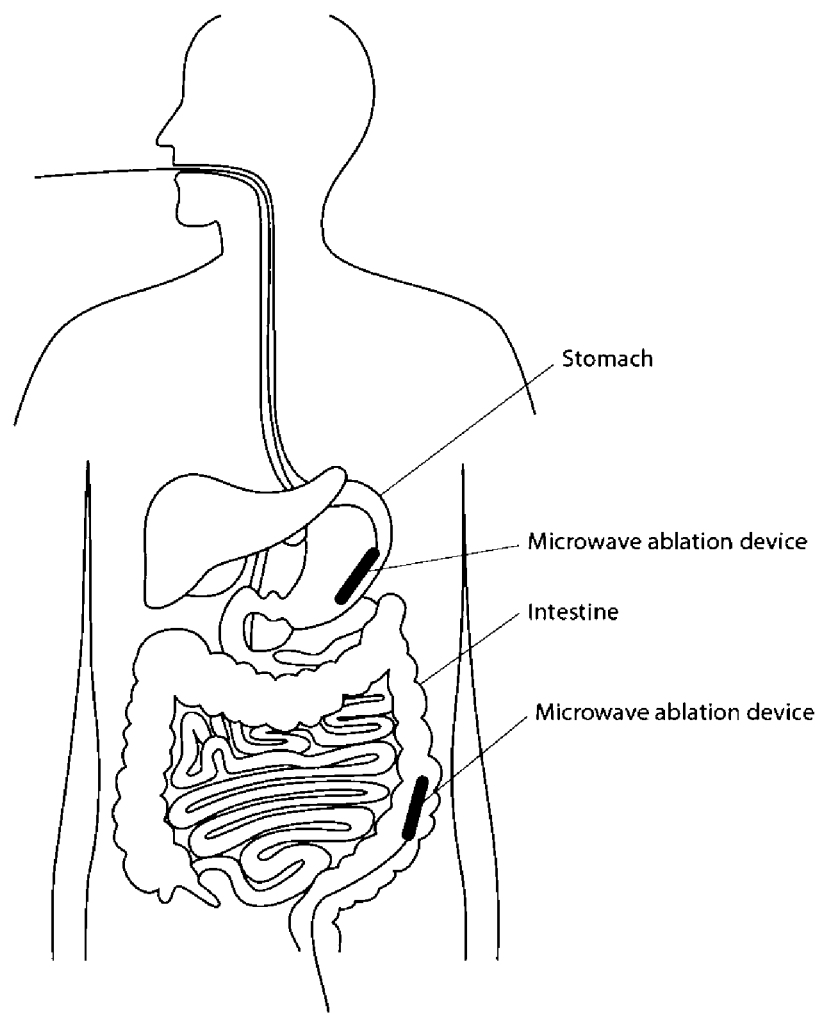
FIG. 28 is a diagram of an example microwave non-thermal ablation device as used treating the gastrointestinal tract.
Figure 29:
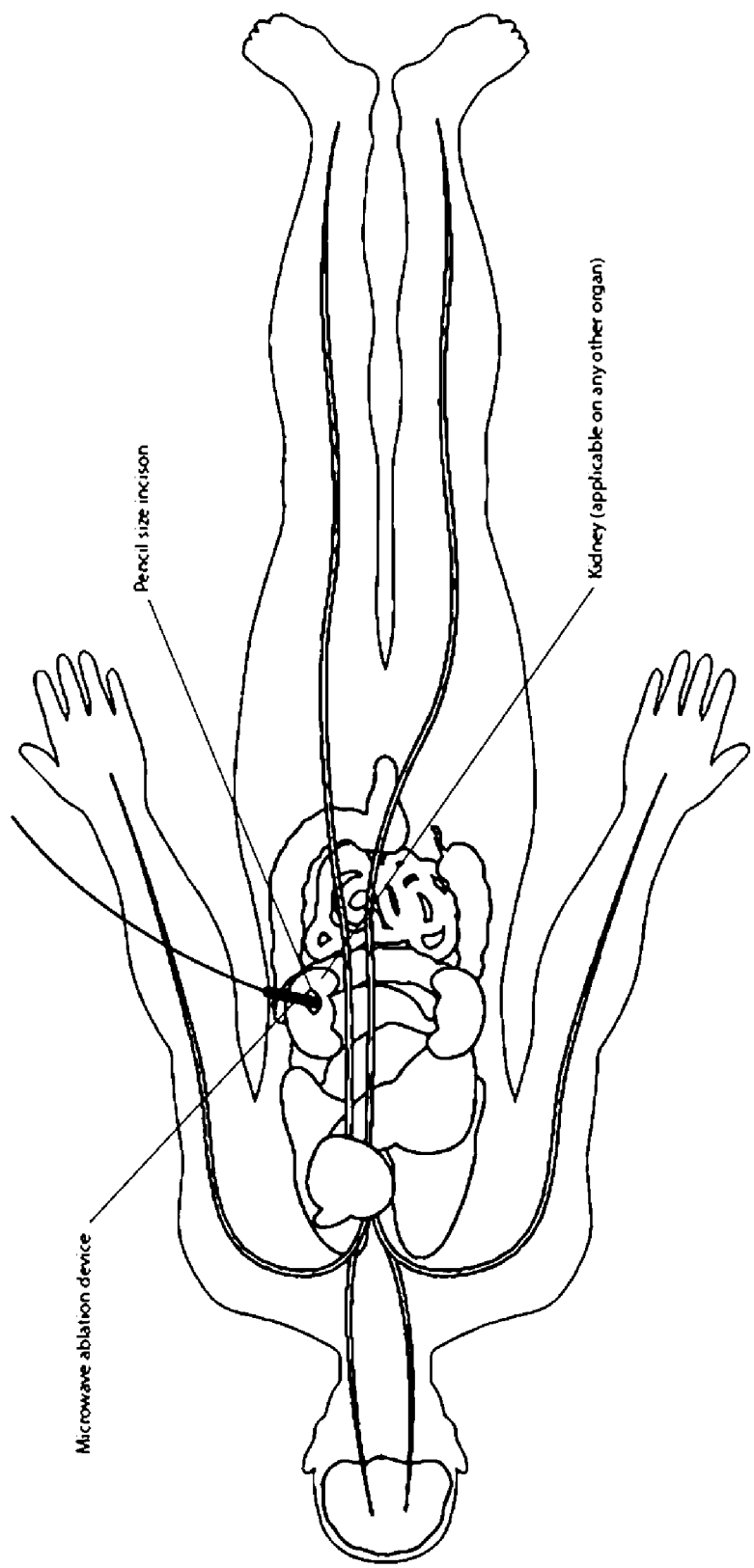
FIG. 29 is a diagram of an example microwave non-thermal ablation device as used laparoscopically to treat parts of the body.

FIG. 27 illustrates a microwave non-thermal ablation device for treating the respiratory tract. For example, microwave ablation device may be the flexible microwave surgery device of FIGS. 25a-b or FIG. 26. FIG. 28 illustrates a microwave non-thermal ablation device for treating the gastrointestinal tract. For example, microwave ablation device may be the flexible microwave surgery device of FIGS. 25a-b or FIG. 26. FIG. 29 illustrates a microwave ablation device with a pencil size incision for treating different parts of body such as kidney, liver, and bone.

Embodiments of the disclosed subject matter are directed to devices and methods for the use of non-thermal effects of microwave energy.

In one embodiment, a process and setup for effective controlling the temperature of a target material while subject to pulsed microwave irradiation and optionally simultaneous or phased irradiation by an ion or an ionizing photon beam comprises:

real-time, and in situ or indirect measurements of the temperature of the target (where the microwave effects are required) and its surrounding (where the microwave radiation could provide unwanted damages) keeping them at a desired level by a combination of the following described cooling methods (for the target and/or the surrounding matrix around the target) and by generating microwave pulses with appropriate variable pulse timings (with microwave pulse widths from microseconds to several seconds) and sequences in response to the temperature of the target;

A) Placing the target in a chamber constructed of an efficient heat exchange material, and preferably a low interaction with microwave radiations, comprised of an inner sample chamber and an outer cooling sheath, as well as sufficient ports for the coolant inlet and outlet, and all the sensor probes for measuring the temperature and any electromagnetic properties and circulating or flowing a coolant through the cooling sheath of the sample chamber and passing it through an appropriate cooling system and controlling its temperature and flow; or B) circulating or flowing a coolant through the sample chamber such that it is in direct contact with the target and optionally passing it through an appropriate cooling system and optionally controlling its temperature or flow, or;

C) circulating a coolant through the sample that goes through an endothermic phase transition to absorb heat from the sample for this phase transition; or D) immersing the target chamber in a large fluid, or solid matrix, or an air flow, or a boiling liquid with appropriate boiling point based on target temperature (to remove the heat by boiling) capable of acting as an efficient heat sink and thermal conductor that regulates the temperature of the target while preferably having a low interaction with microwave radiation or circulating or flowing a liquid target or any semi-liquid target such as suspensions and mixtures of liquid (as a carrier) and fine solids material, through the microwave cavity and optionally passing it through a cooling system outside of microwave radiation zone and optionally controlling its temperature or flow; or E) a delivery system such as a conveyor belt to flow any kind of target through the microwave cavity or passed the region under intense electric or magnetic field by the microwave antennas, optionally passing it through a cooling system outside of microwave radiation zone and optionally controlling its temperature or flow; or F) placing the sample chamber or the target, the tubing, and the probes into a microwave cavity or in the region of maximum electric field or magnetic field generated by a combination of antennas and irradiate the target by using the pulsed microwave generating system (with pulse widths in the range of microseconds to several seconds) which has sufficient ports to accommodate the related tubing, probes, interlocks and optical and other spectroscopic ports, and a covering microwave absorbing material (in the case of antennas) which is transparent to particle beams and prevent any microwave leakage if the application is a surface application or external to an inner body (such as human body);

wherein the source of the microwave pulses could be but not limited to microwave tube (such as magnetron, klystron, traveling-wave tube, and gyrotron) or a solid-state device (such as field-effect transistor, tunnel diode, Gunn diode, and IMPATT diode) or a combination of multiple sources;

wherein the coolant could be but not limited to liquid or expanding gaseous form of $CO_2$, nitrogen or argon or helium, aqueous solutions such as aqueous ethylene glycol, salt solutions, ionic liquids, deep eutectic solvents, solid or cooled vapor form of carbon dioxide, silicone oils, and compounds containing hydroxyl group or it could be a mixture of fluids that go through endothermic phase transitions at different temperatures.

The control over pulse timing and sequences via a feedback loop and programing allows to irradiate the target with strong microwave pulses (several kilowatts) even at very low subzero Celsius temperatures (at any temperature).

In another embodiment, a process and setup for effective controlling the temperature of a target material, such as but not limited to gas samples, liquid samples, solid samples, biological material, body tissue (either in the body, external of the body or on the surface) while subject to pulsed microwave irradiation (with the pulse widths in the range of microseconds to several seconds) and optionally simultaneous or phased irradiation by an ion or an ionizing photon beam comprises:

real-time, and direct or indirect measurements of the temperature of the target and its surrounding and keeping them at a desired level by a combination of one or more of the following described cooling methods and generating microwave pulses with appropriate variable pulse timings and sequences in response to the temperature of the target:

cooling the target utilizing a laser cooling technique such as Doppler cooling, with optional magnetic trapping of the target, or cooling the sample by a magnetocaloric effect refrigeration system, wherein the cooling process can happen before entering the microwave radiation chamber, or after exiting the microwave radiation chamber, or inside the microwave cavity;

cooling the target by means of the microwave cooling method which is based on molecular excitation in a rotational transition when they are subject to microwaves followed by emission to an excited rotational state.

In another embodiment, a process using the previously described methods as well as appropriate temperature (E.g. under 10 C for certain gram positive, and at 45+/−2 C for certain gram negative bacteria) and salt concentration (in the range of 0.5 to 1 percent), using NaCl and all other edible and non-toxic salts and ionic liquids, for disinfecting or sterilizing liquids such as but not limited to fruit juice and milk, and semi-liquid foods such as tomato sauce and salad sauces, and a mixture of liquid and solid foods such as but not limited to broth, or solid food, raw and processed foods including but not limited to meats, seafood, and vegetables or other solid material (such as but not limited to objects in hospitals that require disinfection) to reduce or eliminate microbial contamination by treating the sample to sufficient non-thermal intense pulsed microwave radiations (this could be even more than 1000 W), while reducing or eliminating undesired thermal effects such as cooking of raw foods, wherein the microwave disinfecting effects are optimized at certain temperatures and the best conditions are either above room temperature or bellow depending on the type of microbes due to interaction of electromagnetic field of the microwaves with the microbes, and wherein the pulse sequence also allows an intense pulse to kill a fraction of microbes, followed by a weak pulse to probe the kill rate due to the change in real part of the permittivity of the material due to killed microbes, wherein the change in permittivity is probed via a return microwave probe which is different in a volume based on the concentration of microbes.

In some embodiments, this pump-probe method is used to continue irradiation till the microbes are reduced under a threshold level required.

In some embodiments, the process of disinfecting or sterilizing comprises:

using a microwave delivery system such as an array of needle shape microwave antennas to penetrate the sample, wherein the array of antennas can generate pulsed microwaves, the needle shape antenna acts as a heat absorbent to cool down the sample;

optionally applying airflow, expanding gas, cold gas, or liquefied gas or a fluid that goes through an endothermic phase transition at the required temperature, for cooling the sample;

optionally, using one or more methods according the previously described embodiments.

In another embodiment, a method and device for thermal pulsed microwave treating of a target tissue by irradiating it with pulsed microwave radiations and optionally simultaneous or phased irradiation by an ion or an ionizing photon or particle beam comprises:

real-time, and in situ or indirect measurements of the temperature of the target and its surrounding and keeping it at a desired level by generating high power microwave pulses (order of magnitude of kW and with pulse widths in the range of microseconds to several seconds pulses) with appropriate variable pulse timings in response to the temperature of the target to keep the temperatures at any desired temperature, wherein the microwave pulses can be used in conjunction with particle beams;

optionally cooling the target (if needed) and the surrounding non-target tissue by using a cooling fluid circulating around the tissue or spraying on the tissue, or by using a thermoelectric device such as Peltier applied on the tissue to minimize the peripheral damage by keeping the non-target tissue at close to the body temperature;

wherein the microwave pulses are generated by one or an array of impedance-matched monopole microwave antennas and the antenna may be moved and placed in a different location of tissue after treatment of one part of tissue, and the device has sufficient ports to accommodate the related tubing, probes, interlocks and optical and other spectroscopic ports, and a covering microwave absorbing material circulating around the antennas, the transport component has a transparent window to particle beams and prevent any microwave leakage if the application is a surface application or external to an inner body (such as human body), and there is a microwave sensor outside the target region that is incorporated within the safety electronic system to automatically shut down the microwave source if the microwave radiation leakage is above a certain threshold via the interlock system;

treating the target tissue with a particle beam, during, after, or prior to the microwave therapy; and simultaneous or time delayed irradiating the target with ionizing radiation (with negative or positive time delays).

In another embodiment, a method and device for non-thermal pulsed microwave treating of a target tissue by irradiating the target tissue with pulsed microwave radiations and optionally simultaneous or phased irradiation by an ion or an ionizing photon or particle beam comprises:

in situ, and direct or indirect measurements of the temperature of the target and surrounding keeping them at a desired level by generating microwave pulses (with the pulse widths in the range of microseconds to several seconds) with appropriate variable pulse timings and pulse sequences in response to the temperature of the target to irradiate the target with strong microwave pulses at any desired temperature, wherein this technique is used in either open surgery or laparoscopic surgery;

use non-thermal microwave effects applying pulsed microwaves and cooling systems;

optionally cooling the target or the surrounding non-target tissue by using a cooling fluid circulating around the tissue or spraying on the tissue, or by using a thermoelectric device such as Peltier applied on the tissue to minimize the peripheral damage by keeping the non-target tissue at close to the body temperature;

optionally using combined non-thermal microwave and cryosurgery to apply the cold materials such as but not limited to cold gases, liquid nitrogen, or other liquefied gases on the target through any kinds of delivery system such as spraying to increase the exposure area for treatment;

optionally using a needle shape microwave antenna, which can also act as a heat absorbent to prevent heating the target surrounding;

optionally, spraying compressed gas, cold gas, or a liquefied gas for cooling the target or its surrounding;

optionally, treating the target tissue with a particle beam, and or laser beam during, after, or prior to the microwave therapy, optionally by inject a salt or ionic liquid or a metallic or magnetic nanoparticle into the tissue that contains tumor to increase the efficiency of microwave non-thermal or localize the specific thermal effects due to the movements of the charges and to combine microwave, ionizing beam and laser therapy by making use of excess transient hole formation to cause in situ oxidization of biomolecules in the cancer cells, wherein the microwave pulses at certain temperatures provide enhancing effects of the ionizing radiation therapeutic effects by increasing certain reactive species and removing others to provide synergistic microwave and ionizing radiation therapies that can be optimized by our device based on solidity of the tumor;

optionally apply a cathode on the target tissue and an anode on the surrounding tissue to produce a current of electrons in the tissue to increase the efficiency of microwave non-thermal effects wherein the timing of the electron pulses would be in respect to the timing of the microwave pulses.

In another embodiment, a pulsed microwave method and device for laparoscopic and percutaneous surgeries comprises:

real-time, and in situ or indirect measurements of the temperature of the target and keeping it at a desired level by a combination of the cooling methods and generating microwave pulses with appropriate variable pulse timings and pulse sequences in response to the temperature of the target to irradiate the target with strong microwave pulses at kW level at any desired temperatures including condition required by cryosurgery to use either NTME or controlled thermal effect, wherein the NTME will take advantage of increased conductivity, water content, salt concentration, and capacitance and modified electrochemical properties of cancer cells compared to healthy cells;

a microwave antenna, an outer sheath and two or more inlet and outlet pipes for cooling purposes;

inlet and outlet pipes are used to deliver any liquid or gas flow to the target tissue to cool it down;

a thermometer such as optical fiber-based ones at the tip to measure the temperature of the target;

a microwave waveguide applied directly on the outer layer of the target tissue or skin to deliver microwave radiations;

optionally using tiny tubes to spray any cold gas or liquid for cooling purposes or insert them into the target if possible;

optionally using a microwave lens made of material such as left-handed material to focus microwaves at a smaller area;

optionally placing some metallic needles inside the target organ between the target part and the healthy part to act as a Faraday cage to attenuate microwaves and to prevent microwaves penetrate further into the healthy part. The needles could also be hollow to circulate a flow for cooling purposes;

optionally inject a salt, an ionic liquid or nanomaterial into the tissue to increase the efficiency of microwave non-thermal effects due to the movements of the charges and magnetic interactions;

irradiating the target with an ion beam simultaneously or in time delayed fashion (with negative or positive time delays) using certain gold nanoparticles stabilized by anti-microbial ionic liquids to tune the ionizing radiation effect and to prevent infection followed by microwave surgery and ionizing radiation.

In another embodiment, a pulsed microwave method and device for treating large targets comprises:

real-time, and in situ or indirect measurements of the temperature of the target and keeping it at a desired level by generating microwave pulses with appropriate variable pulse timings and pulse sequences in response to the temperature of the target to allow irradiating the target with strong microwave pulses even at any desired temperatures to use NTME to take advantage of increased conductivity, water content, salt concentration, and capacitance and modified electrochemical properties of cancer cells compared to healthy cells;

wherein the microwave pulses are generated by one or an array of impedance-matched monopole microwave antennas and inserting them into the body around the target area for laparoscopic surgery;

optionally insert two or more tiny inlet and outlet tubes in the middle of the target for cooling purposes;

optionally simultaneous irradiating the target with ionizing radiation.

In another embodiment, a pulsed microwave method and device for treating different types of diseases including cancers such as but not limited to lung, tracheal and gastric malignancies comprises:

real-time, and in situ or indirect measurements of the temperature of the target and keeping it at a desired level by a combination of the following described cooling method and generating microwave pulses with appropriate variable pulse timings and pulse sequences in response to the temperature of the target to allow irradiating the target with strong microwave pulses even at any desired temperatures to use NTME or controlled thermal effect, wherein the NTME will take advantage of increased conductivity, water content, salt concentration, and capacitance and modified electrochemical properties of cancer cells compared to healthy cells;

a flexible impedance-matched microwave antenna inside a flexible sheath, wherein the sheath has some inlet and outlet holes for cooling purposes by using a cold gas or a liquid and the cooling material is in direct contact with the tissue and wherein inlet holes are used for injecting cooling material and outlet holes are connected to a suction device to drain the cooling material;

a pressure regulator to prevent increasing the cooling gas pressure inside the body above a threshold, wherein, a safety pressure sensor is operable to cut off the microwave source and inlet gas when the pressure exceeds a certain level;

optionally, simultaneous irradiating the target with ionizing radiation.

In another embodiment, a pulsed microwave medical therapy tool comprises:

real-time, and in situ or indirect measurements of the temperature of the target and keeping it at a desired level by a combination of the following described cooling method and generating microwave pulses with appropriate variable pulse timings and sequences in response to the temperature of the target to irradiate the target with strong microwave pulses even at any desired temperatures to use NTME;

a microwave antenna in the middle of the tool;

a cylindrical cooling jacket at the top with inlet and outlet to circulate cooling liquid in order to control the temperature of the target tissue and cool down the adjacent tissues to body temperature.

In some embodiments, a microwave treatment method and device further comprises:

injecting materials into the target tissue or the blood stream that could interact with microwaves, such as but not limited to special ionic liquids, salt solutions, amino acids, ionic penetrating peptides, metallic nanoparticles, super paramagnetic polymers and composites and non-toxic ferromagnetic or non-toxic paramagnetic materials;

wherein the injected materials have affinity for malignant cells more than healthy cells;

adjusting the timing of irradiation with microwave referenced to time of injection to have maximum effect on cancer tissues.

In another embodiment, a complementary microwave treatment method and device for affected tissues for a combination of real-time imaging techniques that lead to producing charged species, with exploiting those charged species in order to enhance the microwave effects comprises:

real-time imaging the tumor and the surrounding tissue to pinpoint the tumor and monitor the microwave therapy process to change the location or the direction of the microwave source accordingly to compensate for the movement of the tumor during the microwave therapy, wherein this may be controlled automatically by a computer, or manually and including imaging methods such as but not limited to CT scan, PET scan and any local spectroscopic probe;

exploiting the ionization radiation of CT scan and X-ray imaging to increase the charge species inside the tumor and enhance the microwave effects;

optionally for increasing the ionizing effect, additional localized ionizing radiations on the tumor may be applied during the microwave therapy; and a combination of real-time PET imaging during microwave therapy comprising of injecting radioactive sugar analog materials which are used in PET imaging such as fludeoxyglucose (FDG), so that they can be absorbed preferentially by tumor cells and decay to generate charged particles such as positrons, wherein the charged particles may generate high energy photons and lead to generate more charged species to enhance microwave effects.

In another embodiment, the previously described medical microwave therapies as used for treating tumors to change the expression level of non-classical MHC-I molecules on the surface of tumor cells so that lymphocytes could attack those tumor cells.

In some embodiments, a process using the previously described methods involving the enhancement of non-thermal microwave effects in chemical and materials chemistry processes and reactions at any required temperature (as cold as required), in materials manufacturing and processing comprises:

controlling the temperature of the reaction media while exposing the media to non-thermal pulsed microwave irradiation at any required set temperature while having any required microwave power up to order of magnitude of kW, resulting in enhanced, or atypical reaction products as compared to purely thermal products;

a microwave pulse triggered polymer shape change or trigger for making molecular machines at any required temperature using microwave pulse and cooling systems;

controlling ionic and radiation chemistry based synthetic methods by microwave pulses at any required high or low temperatures (any lower than 0 C is possible) differently for liquid and solid based methods.

In some embodiments, the previously described methods and devices decrease the electron-hole recombination in semiconductor or solid-state devices as such increasing the efficiency in solar cells, photodiodes, photocatalysts, DPSSs, quantum cascade lasers (QCLs).

In some embodiments, an in situ spectroscopic analysis probe is used with the previously described methods or other temperature and pulse control methods and additionally the spectroscopic analysis under pulsed microwave radiation is undertaken optionally including: UV-Visible spectroscopy, Infra-red spectroscopy, Nuclear Magnetic Resonance spectroscopy, ultrasound spectroscopy, Raman spectroscopy, mSR, small angle X-ray scattering, electrochemical-optical, Crenkov spectroscopy and wide-angle X-ray scattering.

In some embodiments, an external magnetic field generated by a permanent magnet or an electromagnet can be applied on the sample to allow investigation NTME in situ at the same temperature and environment (same light intensity, same medium, same geometry, etc.) as thermal method (microwave off).

In another embodiment, a pulse radiolysis or flash photolysis system, where free radical and transient intermediates are produced by ionizing radiation pulses, comprises:

a temperature control of the system of study by pulse radiolysis or flash photolysis performed by the previously described methods; and reactions of some free radicals and reactive intermediates as well as negative and positive ions are controlled by electric and magnetic fields (for free radicals, or paramagnetic species) of microwave under controlled temperature by the previously described methods.

In another embodiment, a method for synthesis of superior alloys and ceramics, comprises:

using rapid high intensity microwave pulses for metal and ceramic powders, the heating can be done under controlled temperatures of the target and keeping it at a desired level by generating microwave pulses with appropriate variable pulse timings and sequences in response to the temperature of the target to control grain-boundary diffusion and volume diffusion;

followed by optionally cryocooling;

rotation/displacement motion of the target by a motor in between pulses at appropriate times to provide consistent and homogenous heating to prevent stress in the material by moving the target in a way that the maximum electric field is moved to a different spot in the target by each move between the pulses to allows irradiating the target with strong microwave pulses at a desired temperature to prevent cracking the targets that have been unsuccessful due to lack of temperature control and existence of temperature gradients across the sample.

In some embodiments, synthesis of polymer structures is achieved using rapid microwave pulses and optionally ionizing radiation followed by immediate rapid cryocooling.

In some embodiments, the presence of oxygen molecules is exploited as paramagnetic molecules in lungs so that the magnetic fields of microwaves could interact with them to have the maximum localized magnetic field by the adjustment of the microwave system.

In another embodiment, a method for microwave sintering under controlled temperatures of the target, comprises:

a combination of the previously described cooling methods, and generating microwave pulses with appropriate variable pulse timings and sequences in response to the temperature of the target to allows irradiating the target with strong microwave pulses at a desired temperature to prevent cracking the targets such metal oxides similar to those that contain $ZrO_2$ to allow for efficient applications of microwave sintering, drying and digestion for nuclear fuel reprocessing and developing novel material for different applications.

In some embodiments, the microwave pulse width and pulse timing is adjusted according to in situ dielectric measurements of the tissue.

In another embodiment, a method of treating a target material, comprises:

placing the target material in a chamber constructed of an efficient heat exchange material having a low interaction with microwave radiation, the chamber comprising an inner sample chamber, an outer cooling sheath, a coolant inlet, a coolant outlet, at least one sensor probe configured to measure the temperature, and at least one sensor probe to measure electromagnetic properties;

circulating a coolant through the outer cooling sheath of the sample chamber and a cooling system configured to regulate the coolants temperature and rate of flow;

placing the sample chamber into a microwave cavity;

irradiating the target material with pulsed microwave radiation;

measuring the temperature of the target material; and controlling the circulation of the coolant to maintain the measured temperature of the target material.

In another embodiment, the microwave system can also be pulsed to allow binning of the spectroscopic and microscopic, and all other physicochemical properties data, through fast pulses of electromagnetic radiation during both the microwave ON and OFF states. This would enable improved signal to noise ratios over multiple scan events as well as an improved understanding of the system behavior under non-thermal microwave effects by simultaneously observing the system spectroscopically with and without microwave irradiation at almost exactly the same temperature and temperature profile during microwave off and microwave on with an average temperature error of less than 2 percent. This has not been available based on previous teachings. These online measurements serve as on line feedback to enhance the microwave applications in materials chemistry, chemical synthesis, industrial applications and radiation therapy, including all concurrent therapies, with one of the concurrent therapies being microwave therapy, by making maximum microwave effects on the target with minimal effects on the surroundings and therefore in the case of radiation therapy or microwave ablations it makes minimum collateral damage to the surrounding tissues. Some of the measurements that can be done in such time resolved manner are such as but not limited to optical and magnetic spectroscopic methods, microwave energy, electric field, magnetic field, dosimetry, Cerenkov spectroscopy (measuring the Cerenkov emission from a sample in case of ionizing irradiation), microscopy and, PET.

In some embodiments, the method includes using the previously described methods to treat a wine, brandy or any other wine derived beverages, whose organoleptic properties can be enhanced through the aging reactions including but not limited to esterification, resulting in artificially aged wine with desired organoleptic properties.

In some embodiments, the previously described processes may be to used treat biological samples, including microorganisms, cells, and tissues to induce non-thermal biological responses to microwave radiation, such as cell signaling, mutations, enhanced or muted effects to stimuli etc.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A method of controlling the temperature of a target material while subjecting the material to microwave irradiation, comprising:

measuring the temperature of the target and its surroundings;

applying a variable length microwave pulse to the target; and means of transporting the microwave radiation that allows microwave field at the target in which the microwave has either its maximum electric field intensity over the area of the target with least magnetic field intensity over the same area or its maximum magnetic field intensity over the area of the target with least electric field intensity over the area;

actively cooling the target; and adjusting the variable length microwave pulse, pulse sequence, pulse shapes, and using phase encoding and the active cooling of the target and its surrounding dependent on the measured temperature to achieve a desired temperature.

2. The method of claim 1, wherein actively cooling the target consists of at least one of circulating a coolant near the target, circulating a coolant around a chamber containing the target, circulating a coolant through the target, cooling a chamber housing the target, cooling the target using a laser cooling technique, and moving the target through the variable length radiation pulse.

3. The method of claim 1, wherein a source of the microwave pulses is at least one of one of a magnetron, klystron, traveling-wave tube, gyrotron, a field-effect transistor, tunnel diode, and a Gunn diode.

4. The method of claim 1, wherein the coolant is selected from the group consisting of but not limited to liquid carbon dioxide, expanding gaseous carbon dioxide, nitrogen, argon, helium, ethylene glycol, salt solutions, ionic liquids, deep eutectic solvents, solid carbon dioxide, cooled vapor carbon dioxide, silicone oils, compounds containing hydroxyl group, and mixtures of fluids that go through endothermic phase transitions at different temperatures.

5. The method of claim 1, wherein the target is a food.

6. The method of claim 5, wherein the food is selected from the group consisting of but not limited to fruit juice, milk, tomato sauce, salad sauce, broth, solid food, raw food, meats, seafood, and vegetables, and wherein the radiation pulse is sufficient to reduce microbial contamination without cooking the food.

7. The method of claim 6, wherein the food is cooled using a non-toxic coolant and the electric field and magnetic field effects of the microwave are enhanced using a nontoxic salt, ionic liquid, or magnetic material.

8. The method of claim 1, wherein the microwave radiation is delivered through an array of microwave needle antennas or at least one antenna.

9. The method of claim 1, wherein the target is a biological tissue.

10. The method of claim 9, further comprising simultaneously irradiating the target with a high energy ion, an ionizing photon, or an ionizing or magnetic particle beam and means of a transport system to transfer antimicrobial electric field or magnetic field effect enhancer materials or radiosensitizers or antimicrobial material for shielding such fields or effects.

11. The method of claim 10, wherein irradiating the target with an ion, an ionizing photon, or ionizing or magnetic particle beam occurs between pulses of the microwave.

12. The methods of claim 11, wherein the microwave pulses are generated by at least one monopole microwave antenna or by an array of microwave needle antennas.

13. The method of claim 9, wherein the microwave pulse is delivered laparoscopically, and means for using a microwave absorbing shield and incorporating interlock safety systems are provided.

14. The method of claim 9, further comprising applying a microwave waveguide directly on the outer layer of the target tissue or skin to deliver the variable length microwave pulse sequence, providing the means of a microwave absorbing shield, incorporated interlock safety systems, and providing the means to transfer antimicrobial electric field or magnetic field effect enhancer materials or radiosensitizers or antimicrobial material for shielding such fields or effects.

15. A non-thermal microwave device, comprising:
a variable pulse width microwave source operable to provide a variable width microwave pulse, with added possibility of setting the pulse sequence, pulse shapes, and phase encoding, to a target;
a microwave transport system that allows microwave field at the target in which the microwave has either its maximum electric field intensity over the area of the target with least magnetic field intensity over the same area or its maximum magnetic field intensity over the area of the target with least electric field intensity over the area;
a temperature monitoring probe operable to measure the temperature of a target and its surrounding;
a transport system for flow of additional material to the target or its surroundings;
a cooling system operable to control the temperature of the target; and
an electronic control circuit operable to adjust pulses properties and the cooling system to maintain a temperature measured by the temperature monitoring probes, the flow of additional materials, and the safety systems such as interlocks.

16. The non-thermal microwave device of claim 15, wherein the microwave source comprises an array of microwave antenna or at least one monopole microwave antenna.

17. The non-thermal microwave device of claim 15, further comprising an imaging device operable to image the target, in which the imaging species has the means to enhance microwave effects locally on target and therefore act as a microwave focusing lens.

18. The non-thermal microwave device of claim 15, wherein the target is selected for transformation from the group (in any state of the material) consisting of a chemical reactant, a biological sample, a food, a polymer, a semiconductor, a surface, a photo catalyst, a solar panel and an industrial waste.

19. The non-thermal microwave device of claim 15, wherein the target is an alloy, ceramic or the precursors of an alloy or ceramic.

20. A pulsed microwave tool comprising:
one or a set of temperature probes for real-time, and in situ or indirect measurements of a temperature of a target and its surrounding;
a cooling system for cooling the target and its surrounding;
a microwave generator operable to generate a variable pulse width microwave with appropriate variable pulse timings and sequences in response to the temperature of the target and its surrounding;
a microwave wave guide, antenna or a set of microwave antennas in the middle of the tool;
a cylindrical cooling jacket at the top with inlet and outlet to circulate cooling liquid in order to control the temperature of the target and cool down material adjacent the target; and
means for transport of ionizing irradiation and probe lights.

21. A method of measuring the effects of microwave radiation on a target that could provide the feedback to control microwave pulses applied for different applications such as but not limited to radiation therapy, surface modification of material, in situ, comprising:
measuring the temperature of the target;
applying a variable length microwave pulse to the target;
actively cooling the target;
adjusting the variable length microwave pulse, pulse sequence, pulse shapes, and using phase encoding and the active cooling of the target dependent on the measured temperature to achieve a desired temperature profile; and when the temperature and temperature profile of the target with microwave on pulse and microwave off between the two microwave pulses are the same within a set threshold;
adjusting the timing circuit for the case of a pulsed probe to positive or negative time delays with respect to microwave pulse;
recording at least one observed characteristic of the target immediately after applying the variable length microwave pules in one channel;
recording at least one observed characteristic of the target during the application of the variable length microwave pulse in another channel; and provide a pump probe time resolved data in the case of pulsed probe with adjusted time delays.

* * * * *